(12) United States Patent
McBride et al.

(10) Patent No.: US 7,597,876 B2
(45) Date of Patent: *Oct. 6, 2009

(54) METHODS AND COMPOSITIONS FOR IMPROVED F-18 LABELING OF PROTEINS, PEPTIDES AND OTHER MOLECULES

(75) Inventors: William J. McBride, Boonton, NJ (US); David M. Goldenberg, Mendham, NJ (US)

(73) Assignee: Immunomedics, Inc., Morris Plains, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/960,262

(22) Filed: Dec. 19, 2007

(65) Prior Publication Data

US 2008/0170989 A1 Jul. 17, 2008

Related U.S. Application Data

(60) Provisional application No. 60/884,521, filed on Jan. 11, 2007.

(51) Int. Cl.
*A61K 51/00* (2006.01)
*A61M 36/14* (2006.01)
(52) U.S. Cl. .................. 424/1.89; 424/1.11; 424/1.69; 424/1.81; 424/1.85; 424/9.4; 424/9.411; 424/9.42
(58) Field of Classification Search ............... 424/1.11, 424/1.49, 1.65, 1.69, 1.81, 1.85, 1.89, 9.1, 424/9.3, 9.4, 9.5, 9.6, 9.7, 9.8, 9.411, 9.42
See application file for complete search history.

(56) References Cited

U.S. PATENT DOCUMENTS

| | | | |
|---|---|---|---|
| 5,256,395 A | 10/1993 | Barbet et al. | |
| 5,446,147 A | 8/1995 | Kung et al. | |
| 6,019,957 A | 2/2000 | Miller et al. | |
| 6,056,939 A | 5/2000 | Desreux et al. | |
| 6,207,858 B1 | 3/2001 | Chinn et al. | |
| 6,605,615 B2 | 8/2003 | Medina et al. | |
| 6,838,073 B1 * | 1/2005 | Collins et al. | 424/1.69 |
| 6,953,567 B2 * | 10/2005 | Griffiths | 424/1.49 |
| 7,011,816 B2 | 3/2006 | Griffiths et al. | |
| 2005/0136001 A1 | 6/2005 | McBride et al. | |
| 2006/0140858 A1 | 6/2006 | Goldenberg et al. | |
| 2008/0253964 A1 | 10/2008 | McBride et al. | |

FOREIGN PATENT DOCUMENTS

| | | |
|---|---|---|
| WO | 2007027385 | 3/2007 |
| WO | 2008088648 | 7/2008 |

OTHER PUBLICATIONS

Imahori et al. "Fluorine-18-Labeled Fluoroboronophenylalanine PET in Patients with Glioma" J Nucl Med 1998; 39:325-333.

McBride et al. "A new method of labeling peptides and proteins with F-18 via a metal ligand" Abstract #384, J Nucl Med. 2008; 49 (Supplement 1):97P.
McBride et al. "A new method of labeling peptides and proteins with F-18 via a metal ligand", PowerPoint Presentation, 55th SNM Annual Meeting, New Orleans, LA, Jun. 17, 2008.
McBride et al. "A New Method of Labeling Peptides with F-18 Via a Metal Ligand", Abstract #04, Cancer Biother Radiopharm Aug. 2008; 23(4): 514.
McBride et al. "A New Method of Labeling Peptides with F-18 Via a Metal Ligand" Abstract #68, 19th Winter Fluorine Conference (Jan. 11-16, 2009) Abstract Book, p. 32.
McBride et al. "A New Method of Labeling Peptides with F-18 Via a Metal Ligand" PowerPoint Presentation, 19th Winter Fluorine Conference, St. Pete Beach, FL, Jan. 13, 2009.
Wagner, Henry N. "Advancing a Molecular Theory of Disease", J Nulc Med 49(8):15N-34N. (2008).
International Patent Appl. No. PCT/US08/62108 titled "Improved Methods and Compositions for F-18 Labeling of Proteins, Peptides and Other Molecules" filed Apr. 30, 2008.
U.S. Appl. No. 12/343,655 titled "Methods and Compositions for F-18 Labeling of Proteins, Peptides and Other Molecules" filed Dec. 24, 2008.
Cai et al. "Chemistry with [18F]Fluoride Ion" Eur. J. Org. Chem. 2008, pp. 2853-2873.
Mamat et al., "Recent Applications of Click Chemistry for the Synthesis of Radiotracers for Molecular Imaging" Mini-Reviews in Organic Chemistry, 2009, vol. 6, pp. 21-34.
Marik et al. "Click for PET: rapid preparation of [18F]fluoropeptides using CuI catalyzed 1,3-dipolar cycloaddition" Tetrahedron Letters 47 (2006) 6681-6684.
Miller et al. "Synthesis of 11C, 18F, 15O, and 13N Radiolabels for Positron Emission Tomography" Angew. Chem. Int. Ed. 2008, vol. 47, pp. 8998-9033.
Schirrmacher et al. "Recent Developments and Trends in 18F-Radiochemistry: Syntheses and Applications" Mini-Reveiws in Organic Chemistry, 2007, vol. 4, pp. 317-329.

(Continued)

*Primary Examiner*—D L Jones
(74) *Attorney, Agent, or Firm*—Richard A. Nakashima

(57) ABSTRACT

The present application discloses compositions and methods of synthesis and use of F-18 labeled molecules of use, for example, in PET imaging techniques. In particular embodiments, the labeled molecules may be peptides or proteins, although other types of molecules including but not limited to aptamers, oligonucleotides and nucleic acids may be labeled and utilized for such imaging studies. In preferred embodiments, the F-18 label may be conjugated to a targeting molecule by formation of a metal complex and binding of the F-18-metal complex to a chelating moiety, such as DOTA, NOTA, DTPA, TETA or NETA. In other embodiments, the metal may first be conjugated to the chelating group and subsequently the F-18 bound to the metal. In other preferred embodiments, the F-18 labeled moiety may comprise a targetable conjugate that may be used in combination with a bispecific or multispecific antibody to target the F-18 to an antigen expressed on a cell or tissue associated with a disease, medical condition, or pathogen. Exemplary results show that F-18 labeled targetable conjugate peptides are stable in human serum at 37° C. for several hours, sufficient time to perform PET imaging analysis.

21 Claims, 22 Drawing Sheets

OTHER PUBLICATIONS

Ting et al. "Toward [18F]-Labeled Aryltrifluoroborate Radiotracers: In Vivo Positron Emission Tomography Imaging of Stable Aryltrifluoroborate Clearance in Mice" J. Am. Chem. Soc. 2008, vol. 130, pp. 12045-12055.

Ting et al. "Arylfruoroborates and Alkylfluorosilicates as Potential PET Imaging Agents: High-Yielding Aqueous Biomolecular 18F-Labeling" J. Am. Chem. Soc. 2005, vol. 127, pp. 13094-13095.

Karacay et al. "18F labeling of a peptide for PET imaging of receptor-expressing tumors" Abstract # 1567, 2009 SNM Annual Meeting Scientific Abstracts 50(Suppl. 2), p. 318P, May 2009.

McBride et al. "A novel method of radiolabeling peptides with aluminium-fluoride-18 (AIF-18) using various NOTA derivatives" Abstract # 202, 2009 SNM Annual Meeting Scientific Abstracts 50(Suppl. 2), pp. 52P-53P, May 2009.

Schoffelen et al. "Pretargeted immunoPET for imaging colorectal cancer in a mouse model" Abstract # 381, 2009 NM Annual Meeting Scientific Abstracts 50(Suppl. 2), pp. 100P, May 2009.

Wester et al. "Fluorine-18 Labeling of Peptides and Proteins", Review, Ernst Schering Res. Found. Workshop 62:79-111(2007).

\* cited by examiner

SEQUENCE LISTING

<160> NUMBER OF SEQ ID NOS: 2

<210> SEQ ID NO 1
<211> LENGTH: 4
<212> TYPE: PRT
<213> ORGANISM: Artificial
<220> FEATURE:
<223> OTHER INFORMATION: Modified peptide: DOTA-Phe-Lys(HSG)-Tyr-Lys(HSG)-NH2

<400> SEQUENCE: 1

Phe Lys Tyr Lys
1

<210> SEQ ID NO 2
<211> LENGTH: 4
<212> TYPE: PRT
<213> ORGANISM: Artificial
<220> FEATURE:
<223> OTHER INFORMATION: Modified peptide: Ac-Lys(DTPA)-Tyr-Lys(DTPA)-Lys(Tscg-Cys)-NH2

<400> SEQUENCE: 2

Lys Tyr Lys Lys
1

METHODS AND COMPOSITIONS FOR IMPROVED F-18 LABELING OF PROTEINS, PEPTIDES AND OTHER MOLECULES

RELATED APPLICATIONS

This application claims the benefit under 35 U.S.C. §119 (e) of Provisional U.S. Patent Application No. 60/884,521, filed Jan. 11, 2007.

FIELD

In certain embodiments, the present invention concerns a simple method of labeling peptides with F-18, which are of use for in-vivo imaging. The preferred specific activity of the F-18 labeled peptide would be about 1,000 to 2,000 Ci/mmol at the time of administration to the patient. Specific activities that are in the range of 100 to tens of thousands of Ci/mmol would also be of use. Preferably, F-18 labeling is accomplished without need for a purification step to separate unlabeled from labeled peptide.

BACKGROUND

Positron Emission Tomography (PET) imaging provides high resolution and quantitation from the PET images. Peptides or other small molecules can be labeled with the positron emitters $^{18}$F, $^{64}$Cu, $^{66}$Ga, $^{68}$Ga, $^{76}$Br, $^{94m}$Tc, $^{86}$Y, and $^{124}$I to name a few. The positron emitted from the nucleus of the isotope is ejected with different energies depending on the isotope used. When the positron reacts with an electron two 511 keV gamma rays are emitted in opposite directions. The energy of the ejected positron controls the average distance that a positron travels before it is annihilated by hitting an electron. The higher the ejection energy the further the positron travels before the collision with an electron. A low ejection energy for a PET isotope is desirable to minimize the distance that the positron travels from the target site before it generates the two 511 keV gamma rays that are imaged by the PET camera. Many isotopes that emit positrons also have other emissions such as gamma rays, alpha particles or beta particles in their decay chain. It is desirable to have a PET isotope that is a pure positron emitter so that any dosimetry problems will be minimized.

The half-life of the isotope is also important, since the half-life must be long enough to attach the isotope to a targeting molecule, analyze the product, inject it into the patient, allow the product to localize, clear from non-target tissues and then image. If the half-life is too long the specific activity may not be high enough to obtain enough photons for a clear image and if it is too short the time needed for manufacturing, commercial distribution and biodistribution may not be sufficient. F-18 ($\beta^+$635 keV 97%, $t_{1/2}$ 110 min) is one of the most widely used PET emitting isotopes because of its low positron emission energy, lack of side emissions and suitable half-life. The F-18 is produced with a high specific activity. If the F-18 is attached to a molecule which has a very high uptake such as 2-fluoro-2-deoxy glucose (FDG) then specific activity is not as important. However, if one is targeting a receptor with a labeled peptide or performing an immunoPET pretargeting study then the specific activity is important.

Conventional F-18 labeling of peptides involves the labeling of a reagent at high specific activity and then conjugation of the F-18 labeled reagent to the peptide. An example is the labeling method of Poethko et al. (*J. Nucl. Med.* 2004; 45: 892-902) in which 4-[$^{18}$F]fluorobenzaldehyde is first synthesized and purified (Wilson et al, *J. Labeled Compounds and Radiopharm.* 1990; XXVIII: 1189-1199) and then conjugated to the peptide. The peptide conjugate is then purified by HPLC to remove excess peptide that was used to drive the conjugation to completion. The two reactions and purification would not be a problem if F-18 had a long half-life. However the half-life of F-18 is only 2 hr so all of the manipulations that are needed to attach the F-18 to the peptide are a significant burden.

These methods are tedious to perform and require the use of equipment designed specifically to produce the labeled product and/or the efforts of specialized professional chemists. They are not kit formulations that could routinely be used in a clinical setting.

SUMMARY

Fluoride binds to practically all other elements and some of those bonds are relatively stable. Peptides, bearing metal binding ligands, are known to bind radiometals stably and at very high specific activity. The approach utilized in the present method was to first bind the F-18 to a metal and then chelate the F-18 metal complex with a ligand on the peptide. The question was then, which metal (or other element e.g. boron) to choose. The elements in group IIIA (boron, aluminum, gallium, indium, thallium) were the first choice based on a quick search of the literature.

Alternatively, one might attach the atom to the peptide first and then add the F-18. The second approach might work better for a boron fluoride connection.

Aluminum fluoride complexes are reported to be stable in-vitro (Martinez et al, *Inorg. Chem.* 1999; 38: 4765-4660; Antonny et al. *J. Biol. Chem.* 1992; 267: 6710-6718). Aluminum fluoride becomes incorporated into bone and into the enamel of teeth so the complexes can also be stable in-vivo (Li, *Crit. Rev. Oral Biol. Med.* 2003; 14: 100-114).

The skilled artisan will realize that virtually any delivery molecule can be used to attach the F-18 for imaging purposes, so long as it contains derivatizable groups that may be modified without affecting the ligand-receptor binding interaction between the delivery molecule and the cellular or tissue target receptor. Although the Examples below concern F-18 labeled peptide moieties, many other types of delivery molecules, such as oligonucleotides, hormones, growth factors, cytokines, chemokines, angiogenic factors, anti-angiogenic factors, immunomodulators, proteins, nucleic acids, antibodies, antibody fragments, drugs, interleukins, interferons, oligosaccharides, polysaccharides, lipids, etc. may be F-18 labeled and utilized for imaging purposes. Similarly, the types of diseases or conditions that may be imaged is limited only by the availability of a suitable delivery molecule for targeting a cell or tissue associated with the disease or condition. For example, in the case of imaging tumors, any antibody fragment that binds to a tumor-associated antigen could be F-18 labeled and utilized for tumor imaging.

In certain Examples below, the exemplary F-18 labeled peptides may be of use for imaging purposes as targetable constructs in a pre-targeting method, utilizing bispecific or multispecific antibodies or antibody fragments. In this case, the antibody or fragment will comprise one or more binding sites for a target associated with a disease or condition, such as a tumor-associated antigen or an antigen produced or displayed by a pathogenic organism, such as a virus, bacterium, fungus or other microorganism. A second binding site will specifically bind to the targetable construct. Methods for pre-targeting using bispecific or multispecific antibodies are well known in the art (see, e.g., U.S. Pat. No. 6,962,702, the entire contents of which are incorporated herein by reference.)

Similarly, antibodies or fragments thereof that bind to targetable constructs are also well known in the art (Id.), such as the 679 monoclonal antibody that binds to HSG (histamine succinyl glycine). Generally, in pretargeting methods the bispecific or multispecific antibody is administered first and allowed to bind to cell or tissue target antigens. After an appropriate amount of time for unbound antibody to clear from circulation, the e.g. F-18 labeled targetable construct is administered to the patient and binds to the antibody localized to target cells or tissues, then an image is taken for example by PET scanning.

In an exemplary embodiment, a non-peptide receptor targeting agent such as ascorbic acid may be conjugated to DOTA and then labeled with, for example, an F-18 metal complex that binds to DOTA. Such non-peptide receptor targeting agents may include, for example, TA138, a non-peptide antagonist for the integrin $\alpha_v\beta_3$ receptor (Liu et al., 2003, Bioconj. Chem. 14:1052-56). Similar non-peptide targeting agents known in the art that can be conjugated to DOTA, NOTA or another chelating agent for F-18 metal complexes may be utilized in the claimed methods. Other receptor targeting agents are known in the art, such as the somatostatin receptor targeting agent In-DTPA octreotide (TYCO®). As discussed below, an F-18-indium complex could potentially be chelated using DTPA and used for imaging purposes. Other methods of receptor targeting imaging using metal chelates are known in the art and may be utilized in the practice of the claimed methods (see, e.g., Andre et al., 2002, J. Inorg. Biochem. 88:1-6; Pearson et al., 1996, J. Med. Chem. 39:1361-71).

Imaging techniques and apparatus for F-18 imaging by PET scanning are also well known in the art (see, e.g., U.S. Pat. Nos. 6,358,489; 6,953,567; Page et al., Nuclear Medicine And Biology, 21:911-919, 1994; Choi et al., Cancer Research 55:5323-5329, 1995; Zalutsky et al., J. Nuclear Med., 33:575-582, 1992) and any such known PET imaging technique or apparatus may be utilized.

BRIEF DESCRIPTION OF THE DRAWINGS

The following Figures are included to illustrate particular embodiments of the invention and are not meant to be limiting as to the scope of the claimed subject matter.

DETAILED DESCRIPTION

Figure 1:
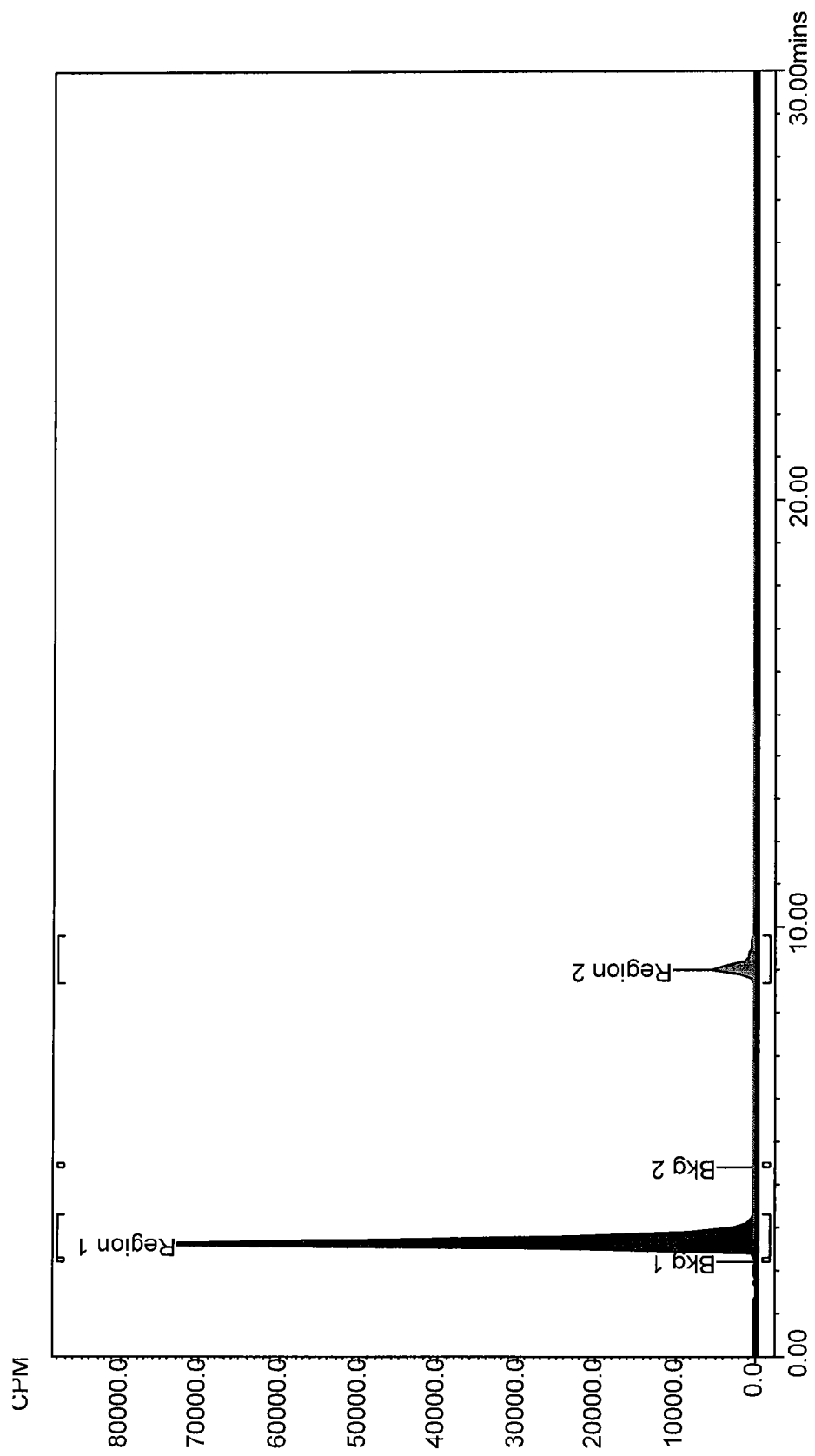
FIG. 1. F-18+IMP 272+AlCl$_3$ heated at 110° C. for 15 min, followed by analysis by reverse phase HPLC.

In the description that follows, a number of terms are used and the following definitions are provided to facilitate understanding of the disclosure herein. Terms that are not explicitly defined are used according to their plain and ordinary meaning.

As used herein, "a" or "an" may mean one or more than one of an item.

As used herein, the terms "and" and "or" may be used to mean either the conjunctive or disjunctive. That is, both terms should be understood as equivalent to "and/or" unless otherwise stated.

As used herein, "about" means within plus or minus ten percent of a number. For example, "about 100" would refer to any number between 90 and 110.

As used herein, a "peptide" refers to any sequence of naturally occurring or non-naturally occurring amino acids of between 2 and 100 amino acid residues in length, more preferably between 2 and 10, more preferably between 2 and 6 amino acids in length. An "amino acid" may be an L-amino acid, a D-amino acid, an amino acid analogue, an amino acid derivative or an amino acid mimetic.

As used herein, the term "pathogen" includes, but is not limited to fungi, viruses (e.g., human immunodeficiency virus (HIV), herpes virus, cytomegalovirus, rabies virus, influenza virus, hepatitis B virus, Sendai virus, feline leukemia virus, Reo virus, polio virus, human serum parvo-like virus, simian virus 40, respiratory syncytial virus, mouse mammary tumor virus, Varicella-Zoster virus, Dengue virus, rubella virus, measles virus, adenovirus, human T-cell leukemia viruses, Epstein-Barr virus, murine leukemia virus, mumps virus, vesicular stomatitis virus, Sindbis virus, lymphocytic choriomeningitis virus, wart virus and blue tongue virus), parasites and bacteria (e.g., *Streptococcus agalactiae, Legionella pneumophilia, Streptococcus pyogenes, Escherichia coli, Neisseria gonorrhocae, Neisseria meningitidis, Pneumococcus, Hemophilis influenzae B, Treponema pallidum*, Lyme disease spirochetes, *Pseudomonas aeruginosa, Mycobacterium leprae, Brucella abortus, Mycobacterium tuberculosis* and *Chlostridium tetani*.)

Targetable Construct Peptides

In certain embodiments, the F-18 labeled moiety may comprise a peptide or other targetable construct. Such targetable constructs can be of diverse structure and are selected not only to elicit sufficient immune responses, but also for rapid in vivo clearance when used within the pre-targeting method and bispecific antibodies (bsAb) or multispecific antibodies. Hydrophobic agents are best at eliciting strong immune responses, whereas hydrophilic agents are preferred for rapid in vivo clearance. Thus, a balance between hydrophobic and hydrophilic character is established. This may be accomplished, in part, by using hydrophilic chelating agents to offset the inherent hydrophobicity of many organic moieties. Also, sub-units of the targetable construct may be chosen which have opposite solution properties, for example, peptides, which contain amino acids, some of which are hydrophobic and some of which are hydrophilic. Aside from peptides, carbohydrates may also be used.

Peptides having as few as two amino acid residues may be used, preferably two to ten residues, and may also coupled to other moieties such as chelating agents. The linker should be a low molecular weight conjugate, preferably having a molecular weight of less than 50,000 daltons, and advantageously less than about 20,000 daltons, 10,000 daltons or 5,000 daltons, including the metal ions in the chelates. More usually, the antigenic peptide will have four or more residues, such as the peptide DOTA-Phe-Lys(HSG)-Tyr-Lys(HSG)-$NH_2$ (SEQ ID NO: 1), wherein DOTA is 1,4,7,10-tetraazacyclododecanetetraacetic acid and HSG is the histamine succinyl glycyl group. Alternatively, the DOTA may be replaced by a NOTA (1,4,7-triaza-cyclononane-N,N',N"-triacetic acid) or TETA (p-bromoacetamido-benzyl-tetraethylaminetetraacetic acid) moiety.

The targetable construct may also comprise unnatural amino acids, e.g., D-amino acids, in the backbone structure to increase the stability of the peptide in vivo. In alternative embodiments, other backbone structures such as those constructed from non-natural amino acids and peptoids.

The peptides used as immunogens are synthesized conveniently on an automated peptide synthesizer using a solid-phase support and standard techniques of repetitive orthogonal deprotection and coupling. Free amino groups in the peptide, that are to be used later for chelate conjugation, are advantageously blocked with standard protecting groups such as a Boc group, while N-terminal residues may be acetylated to increase serum stability. Such protecting groups will be known to the skilled artisan. See Greene and Wuts Protective Groups in Organic Synthesis, 1999 (John Wiley and Sons, N.Y.). When the peptides are prepared for later use within the bsAb system, they are advantageously cleaved from the resins to generate the corresponding C-terminal amides, in order to inhibit in vivo carboxypeptidase activity.

The haptens of the immunogen comprise an immunogenic recognition moiety, for example, a chemical hapten. Using a chemical hapten, preferably the HSG hapten, high specificity of the linker for the antibody is exhibited. This occurs because antibodies raised to the HSG hapten are known and can be easily incorporated into the appropriate bispecific antibody. Thus, binding of the linker with the attached hapten would be highly specific for the antibody or antibody fragment.

Chelate Moieties

In some embodiments, an F-18 labeled molecule may comprise one or more hydrophilic chelate moieties, which can bind metal ions and also help to ensure rapid in vivo clearance. Chelators may be selected for their particular metal-binding properties, and may be readily interchanged.

Particularly useful metal-chelate combinations include 2-benzyl-DTPA and its monomethyl and cyclohexyl analogs. Macrocyclic chelators such as NOTA (1,4,7-triaza-cyclononane-N,N',N"-triacetic acid), DOTA, and TETA (p-bromoacetamido-benzyl-tetraethylaminetetraacetic acid) are also of use with a variety of metals, that may potentially be used as ligands for F-18 conjugation.

DTPA and DOTA-type chelators, where the ligand includes hard base chelating functions such as carboxylate or amine groups, are most effective for chelating hard acid cations, especially Group IIa and Group IIIa metal cations. Such metal-chelate complexes can be made very stable by tailoring the ring size to the metal of interest. Other ring-type chelators such as macrocyclic polyethers are of interest for stably binding nuclides. Porphyrin chelators may be used with numerous metal complexes. More than one type of chelator may be conjugated to a carrier to bind multiple metal ions. Chelators such as those disclosed in U.S. Pat. No. 5,753,206, especially thiosemicarbazonylglyoxylcysteine (Tscg-Cys) and thiosemicarbazinyl-acetylcysteine (Tsca-Cys) chelators are advantageously used to bind soft acid cations of Tc, Re, Bi and other transition metals, lanthanides and actinides that are tightly bound to soft base ligands. It can be useful to link more than one type of chelator to a peptide. Because antibodies to a di-DTPA hapten are known (Barbet et al., U.S. Pat. No. 5,256,395) and are readily coupled to a targeting antibody to form a bsAb, it is possible to use a peptide hapten with cold diDTPA chelator and another chelator for binding an F-18 complex, in a pretargeting protocol. One example of such a peptide is Ac-Lys(DTPA)-Tyr-Lys(DTPA)-Lys(Tscg-Cys)-$NH_2$ (SEQ ID NO:2). Other hard acid chelators such as DOTA, TETA and the like can be substituted for the DTPA and/or Tscg-Cys groups, and Mabs specific to them can be produced using analogous techniques to those used to generate the anti-di-DTPA Mab.

Another useful chelator may comprise a NOTA-type moiety, for example as disclosed in Chong et al. (Rational design and generation of a bimodal bifunctional ligand for antibody-targeted radiation cancer therapy, *J. Med. Chem.*, e-published on Dec. 7, 2007, incorporated herein by reference). Chong et al. disclose the production and use of a bifunctional C-NETA ligand, based upon the NOTA structure, that when complexed with $^{177}$Lu or $^{205/206}$Bi showed stability in serum for up to 14 days.

It will be appreciated that two different hard acid or soft acid chelators can be incorporated into the targetable construct, e.g., with different chelate ring sizes, to bind preferentially to two different hard acid or soft acid cations, due to the differing sizes of the cations, the geometries of the chelate rings and the preferred complex ion structures of the cations. This will permit two different metals, one or both of which may be attached to F-18, to be incorporated into a targetable construct for eventual capture by a pretargeted bsAb.

Methods of Administration

In various embodiments, bispecific antibodies and targetable constructs may be used for imaging normal or diseased tissue and organs (see, e.g. U.S. Pat. Nos. 6,126,916; 6,077,499; 6,010,680; 5,776,095; 5,776,094; 5,776,093; 5,772,981; 5,753,206; 5,746,996; 5,697,902; 5,328,679; 5,128,119; 5,101,827; and 4,735,210).

The administration of a bsAb and an F-18 labeled targetable construct may be conducted by administering the bsAb at some time prior to administration of the targetable construct. The doses and timing of the reagents can be readily devised by a skilled artisan, and are dependent on the specific nature of the reagents employed. If a bsAb-F(ab')$_2$ derivative is given first, then a waiting time of 24-72 hr before administration of the targetable construct would be appropriate. If an IgG-Fab' bsAb conjugate is the primary targeting vector, then a longer waiting period before administration of the targetable construct would be indicated, in the range of 3-10 days. After sufficient time has passed for the bsAb to target to the diseased tissue, the F-18 labeled targetable construct is administered. Subsequent to administration of the targetable construct, imaging can be performed.

Certain embodiments concern the use of multivalent target binding proteins which have at least three different target binding sites as described in patent application Ser. No. 60/220,782. Multivalent target binding proteins have been made by cross-linking several Fab-like fragments via chemical linkers. See U.S. Pat. Nos. 5,262,524; 5,091,542 and Landsdorp et al. Euro. J. Immunol. 16: 679-83 (1986). Multivalent target binding proteins also have been made by covalently linking several single chain Fv molecules (scFv) to form a single polypeptide. See U.S. Pat. No. 5,892,020. A multivalent target binding protein which is basically an aggregate of scFv molecules has been disclosed in U.S. Pat. Nos. 6,025,165 and 5,837,242. A trivalent target binding protein comprising three scFv molecules has been described in Krott et al. Protein Engineering 10(4): 423-433 (1997).

A clearing agent may be used which is given between doses of the bsAb and the targetable construct. A clearing agent of novel mechanistic action may be used, namely a glycosylated anti-idiotypic Fab' fragment targeted against the disease targeting arm(s) of the bsAb. In one example, anti-CEA (MN 14 Ab)× anti-peptide bsAb is given and allowed to accrete in disease targets to its maximum extent. To clear residual bsAb, an anti-idiotypic Ab to MN-14, termed W12, is given, preferably as a glycosylated Fab' fragment. The clearing agent binds to the bsAb in a monovalent manner, while its appended glycosyl residues direct the entire complex to the liver, where rapid metabolism takes place. Then the F-18 labeled targetable construct is given to the subject. The W12 Ab to the MN-14 arm of the bsAb has a high affinity and the clearance mechanism differs from other disclosed mechanisms (see Goodwin et al., ibid), as it does not involve cross-linking, because the W12-Fab' is a monovalent moiety.

Methods for Raising Antibodies

Abs to peptide backbones may be generated by well-known methods for Ab production. For example, injection of an immunogen, such as (peptide)$_n$-KLH, wherein KLH is keyhole limpet hemocyanin, and n=1-30, in complete Freund's adjuvant, followed by two subsequent injections of the same immunogen suspended in incomplete Freund's adjuvant into immunocompetent animals, is followed three days after an i.v. boost of antigen, by spleen cell harvesting. Harvested spleen cells are then fused with Sp2/0-Ag14 myeloma cells and culture supernatants of the resulting clones analyzed for anti-peptide reactivity using a direct-binding ELISA. Specificity of generated Abs can be analyzed for by using peptide fragments of the original immunogen. These fragments can be prepared readily using an automated peptide synthesizer. For Ab production, enzyme-deficient hybridomas are isolated to enable selection of fused cell lines. This technique also can be used to raise antibodies to one or more of the chelates comprising the targetable construct, e.g., In(III)-DTPA chelates. Monoclonal mouse antibodies to an In(III)-di-DTPA are known (Barbet '395 supra).

The targeting antibodies used may be specific to a variety of cell surface or intracellular tumor-associated antigens as marker substances. These markers may be substances produced by the tumor or may be substances which accumulate at a tumor site, on tumor cell surfaces or within tumor cells, whether in the cytoplasm, the nucleus or in various organelles or sub-cellular structures. Among such tumor-associated markers are those disclosed by Herberman, "Immunodiagnosis of Cancer", in Fleisher ed., "The Clinical Biochemistry of Cancer", page 347 (American Association of Clinical Chemists, 1979) and in U.S. Pat. Nos. 4,150,149; 4,361,544; and 4,444,744.

Tumor-associated markers have been categorized by Herberman, supra, in a number of categories including oncofetal antigens, placental antigens, oncogenic or tumor virus associated antigens, tissue associated antigens, organ associated antigens, ectopic hormones and normal antigens or variants thereof. Occasionally, a sub-unit of a tumor-associated marker is advantageously used to raise antibodies having higher tumor-specificity, e.g., the beta-subunit of human chorionic gonadotropin (HCG) or the gamma region of carcino embryonic antigen (CEA), which stimulate the production of antibodies having a greatly reduced cross-reactivity to non-tumor substances as disclosed in U.S. Pat. Nos. 4,361,644 and 4,444,744.

Another marker of interest is transmembrane activator and CAML-interactor (TACI). See Yu et al. Nat. Immunol. 1:252-256 (2000). Briefly, TACI is a marker for B-cell malignancies (e.g., lymphoma). Further it is known that TACI and B cell maturation antigen (BCMA) are bound by the tumor necrosis factor homolog—a proliferation-inducing ligand (APRIL). APRIL stimulates in vitro proliferation of primary B and T cells and increases spleen weight due to accumulation of B cells in vivo. APRIL also competes with TALL-I (also called BLyS or BAFF) for receptor binding. Soluble BCMA and TACI specifically prevent binding of APRIL and block APRIL-stimulated proliferation of primary B cells. BCMA-Fc also inhibits production of antibodies against keyhole limpet hemocyanin and Pneumovax in mice, indicating that APRIL and/or TALL-I signaling via BCMA and/or TACI are required for generation of humoral immunity. Thus, APRIL-TALL-I and BCMA-TACI form a two ligand-two receptor pathway involved in stimulation of B and T cell function.

Exemplary target antigens of use for imaging various diseases or conditions, such as a malignant disease, a cardiovascular disease, an infectious disease, an inflammatory disease, an autoimmune disease, or a neurological disease may include colon-specific antigen-p (CSAp), carcinoembryonic antigen (CEA), CD4, CD5, CD8, CD14, CD15, CD19, CD20, CD21, CD22, CD23, CD25, CD30, CD45, CD74, CD80, HLA-DR, Ia, Ii, MUC 1, MUC 2, MUC 3, MUC 4, NCA, EGFR, HER 2/neu, TAG-72, EGP-1, EGP-2, A3, KS-1, Le(y), S100, PSMA, PSA, tenascin, folate receptor, VEGFR, P1GF, ILGF-1, necrosis antigens, IL-2, IL-6, T101, MAGE, or a combination of these antigens. In particular, antigens may include carcinoembryonic antigen (CEA), tenascin, epidermal growth factor receptor, platelet derived growth factor receptor, fibroblast growth factor receptors, vascular endothelial growth factor receptors, gangliosides, HER/2neu receptors and combinations of these antigens.

After the initial raising of antibodies to the immunogen, the antibodies can be sequenced and subsequently prepared by recombinant techniques. Humanization and chimerization of murine antibodies and antibody fragments are well known to those skilled in the art. For example, humanized monoclonal antibodies are produced by transferring mouse complementary determining regions from heavy and light variable chains of the mouse immunoglobulin into a human variable domain, and then, substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by the publication of Orlandi et al., Proc. Nat'l Acad. Sci. USA 86: 3833 (1989), which is incorporated by reference in its entirety. Techniques for producing humanized Mabs are described, for example, by Jones et al., Nature 321: 522 (1986), Riechmann et al., Nature 332: 323 (1988), Verhoeyen et al., Science 239: 1534 (1988), Carter et al., Proc. Nat'l Acad. Sci. USA 89: 4285 (1992), Sandhu, Crit. Rev. Biotech. 12: 437 (1992), and Singer et al., J. Immun. 150: 2844 (1993), each of which is incorporated herein by reference in its entirety.

Alternatively, fully human antibodies can be obtained from transgenic non-human animals. See, e.g., Mendez et al., Nature Genetics, 15: 146-156 (1997); U.S. Pat. No. 5,633, 425. For example, human antibodies can be recovered from transgenic mice possessing human immunoglobulin loci. The mouse humoral immune system is humanized by inactivating the endogenous immunoglobulin genes and introducing human immunoglobulin loci. The human immunoglobulin loci are exceedingly complex and comprise a large number of discrete segments which together occupy almost 0.2% of the human genome. To ensure that transgenic mice are capable of producing adequate repertoires of antibodies, large portions of human heavy- and light-chain loci must be introduced into the mouse genome. This is accomplished in a stepwise process beginning with the formation of yeast artificial chromosomes (YACs) containing either human heavy- or light-chain immunoglobulin loci in germline configuration. Since each insert is approximately 1 Mb in size, YAC construction requires homologous recombination of overlapping fragments of the immunoglobulin loci. The two YACs, one containing the heavy-chain loci and one containing the light-chain loci, are introduced separately into mice via fusion of YAC-containing yeast spheroblasts with mouse embryonic stem cells. Embryonic stem cell clones are then microinjected into mouse blastocysts. Resulting chimeric males are screened for their ability to transmit the YAC through their germline and are bred with mice deficient in murine antibody production. Breeding the two transgenic strains, one containing the human heavy-chain loci and the other containing the human light-chain loci, creates progeny which produce human antibodies in response to immunization.

Unrearranged human immunoglobulin genes also can be introduced into mouse embryonic stem cells via microcell-mediated chromosome transfer (MMCT). See, e.g., Tomizuka et al., Nature Genetics, 16: 133 (1997). In this methodology microcells containing human chromosomes are fused with mouse embryonic stem cells. Transferred chromosomes are stably retained, and adult chimeras exhibit proper tissue-specific expression.

As an alternative, an antibody or antibody fragment may be derived from human antibody fragments isolated from a combinatorial immunoglobulin library. See, e.g., Barbas et al., METHODS: A Companion to Methods in Enzymology 2: 119 (1991), and Winter et al., Ann. Rev. Immunol. 12: 433 (1994), which are incorporated herein by reference. Many of the difficulties associated with generating monoclonal antibodies by B-cell immortalization can be overcome by engineering and expressing antibody fragments in *E. coli*, using phage display.

A similar strategy can be employed to obtain high-affinity scFv. See, e.g., Vaughn et al., Nat. Biotechnol., 14: 309-314 (1996). An scFv library with a large repertoire can be constructed by isolating V-genes from non-immunized human donors using PCR primers corresponding to all known $V_H$, $V_{kappa}$ and $V_{80}$ gene families. Following amplification, the $V_{kappa}$ and $V_{lambda}$ pools are combined to form one pool. These fragments are ligated into a phagemid vector. The scFv linker, $(Gly_4, Ser)_3$, is then ligated into the phagemid upstream of the $V_L$ fragment. The $V_H$ and linker-$V_L$ fragments are amplified and assembled on the $J_H$ region. The resulting $V_H$-linker-$V_L$ fragments are ligated into a phagemid vector. The phagemid library can be panned using filters, as described above, or using immunotubes (NUNC®; MAX-ISORP®). Similar results can be achieved by constructing a combinatorial immunoglobulin library from lymphocytes or spleen cells of immunized rabbits and by expressing the scFv constructs in *P. pastoris*. See, e.g., Ridder et al., Biotechnology, 13: 255-260 (1995). Additionally, following isolation of an appropriate scFv, antibody fragments with higher binding affinities and slower dissociation rates can be obtained through affinity maturation processes such as CDR3 mutagenesis and chain shuffling. See, e.g., Jackson et al., Br. J. Cancer, 78: 181-188 (1998); Osbourn et al., Immunotechnology, 2: 181-196 (1996).

Another form of an antibody fragment is a peptide coding for a single CDR. CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick et al., Methods: A Companion to Methods in Enzymology 2:106 (1991); Courtenay-Luck, "Genetic Manipulation of Monoclonal Antibodies," in MONOCLONAL ANTIBODIES: PRODUCTION, ENGINEERING AND CLINICAL APPLICATION, Ritter et al. (eds.), pages 166-179 (Cambridge University Press 1995); and Ward et al., "Genetic Manipulation and Expression of Antibodies," in MONOCLONAL ANTIBODIES: PRINCIPLES AND APPLICATIONS, Birch et al., (eds.), pages 137-185 (Wiley-Liss, Inc. 1995).

The bsAbs can be prepared by techniques known in the art, for example, an anti-CEA tumor Ab and an anti-peptide Ab are both separately digested with pepsin to their respective $F(ab')_2$ fragments. The anti-CEA-Ab-$F(ab')_2$ is reduced with cysteine to generate Fab' monomeric units which are further reacted with the cross-linker bis(maleimido) hexane to produce Fab'-maleimide moieties. The anti-peptide Ab-$F(ab')_2$ is reduced with cysteine and the purified, recovered anti-peptide Fab'-SH reacted with the anti-CEA-Fab'-maleimide to generate the Fab'×Fab' bi-specific Ab. Alternatively, the anti-peptide Fab'-SH fragment may be coupled with the anti-CEA $F(ab')_2$ to generate a $F(ab')_2$×Fab' construct, or with anti-CEA IgG to generate an IgG×Fab' bi-specific construct. In one embodiment, the IgG×Fab' construct can be prepared in a site-specific manner by attaching the antipeptide Fab' thiol group to anti-CEA IgG heavy-chain carbohydrate which has been periodate-oxidized, and subsequently activated by reaction with a commercially available hydrazide-maleimide cross-linker. The component Abs used can be chimerized or humanized by known techniques. A chimeric antibody is a recombinant protein that contains the variable domains and complementary determining regions derived from a rodent antibody, while the remainder of the antibody molecule is derived from a human antibody. Humanized antibodies are recombinant proteins in which murine complementarity determining regions of a monoclonal antibody have been transferred from heavy and light variable chains of the murine immunoglobulin into a human variable domain.

A chimeric Ab is constructed by ligating the cDNA fragment encoding the mouse light variable and heavy variable domains to fragment encoding the C domains from a human antibody. Because the C domains do not contribute to antigen binding, the chimeric antibody will retain the same antigen specificity as the original mouse Ab but will be closer to human antibodies in sequence. Chimeric Abs still contain some mouse sequences, however, and may still be immunogenic. A humanized Ab contains only those mouse amino acids necessary to recognize the antigen. This product is constructed by building into a human antibody framework the amino acids from mouse complementarity determining regions.

Other recent methods for producing bsAbs include engineered recombinant Abs which have additional cysteine residues so that they crosslink more strongly than the more common immunoglobulin isotypes. See, e.g., FitzGerald et al., Protein Eng. 10:1221-1225, 1997. Another approach is to engineer recombinant fusion proteins linking two or more different single-chain antibody or antibody fragment segments with the needed dual specificities. See, e.g., Coloma et al., Nature Biotech. 15:159-163, 1997. A variety of bi-specific fusion proteins can be produced using molecular engineering. In one form, the bi-specific fusion protein is monovalent, consisting of, for example, a scFv with a single binding site for one antigen and a Fab fragment with a single binding site for a second antigen. In another form, the bi-specific fusion protein is divalent, consisting of, for example, an IgG with two binding sites for one antigen and two scFv with two binding sites for a second antigen.

Functional bi-specific single-chain antibodies (bscAb), also called diabodies, can be produced in mammalian cells using recombinant methods. See, e.g., Mack et al., Proc. Natl. Acad. Sci., 92: 7021-7025, 1995.

Preferred bispecific antibodies are those which incorporate the Fv of MAb Mu9 and the Fv of MAb 679 or the Fv of MAb MN14 and the Fv of MAb 679, and their human, chimerized or humanized counterparts. The MN14, as well as its chimerized and humanized counterparts, are disclosed in U.S. Pat. No. 5,874,540. Also preferred are bispecific antibodies which incorporate one or more of the CDRs of Mu9 or 679. The antibody can also be a fusion protein or a bispecific antibody that incorporates a Class III anti-CEA antibody and the Fv of 679. Class III antibodies, including Class III anti-CEA are discussed in detail in U.S. Pat. No. 4,818,709.

In certain embodiments, the bsAb F-18 labeled targetable constructs discussed above may be used in intraoperative, intravascular, and endoscopic tumor and lesion detection, biopsy and therapy as described in U.S. Pat. No. 6,096,289.

EXAMPLES

Example 1

F-18 Labeling of Peptide IMP 272

The first peptide that was used was IMP 272
DTPA-Gln-Ala-Lys(HSG)-D-Tyr-Lys(HSG)-NH$_2$  MH$^+$ 1512

Acetate buffer solution—Acetic acid, 1.509 g was diluted in ~160 mL water and the pH was adjusted by the addition of 1 M NaOH then diluted to 250 mL to afford a 0.1 M solution at pH 4.03.

Aluminum acetate buffer solution—A solution of aluminum was prepared by dissolving 0.1028 g of AlCl$_3$ hexahydrate in 42.6 mL DI water. A 4 mL aliquot of the aluminum solution was mixed with 16 mL of a 0.1 M NaOAc solution at pH 4 to provide a 2 mM Al stock solution.

IMP 272 acetate buffer solution—Peptide, 0.0011 g, 7.28× 10$^{-7}$ mol IMP 272 was dissolved in 364 μL of the 0.1 M pH 4 acetate buffer solution to obtain a 2 mM stock solution of the peptide.

Figure 2:
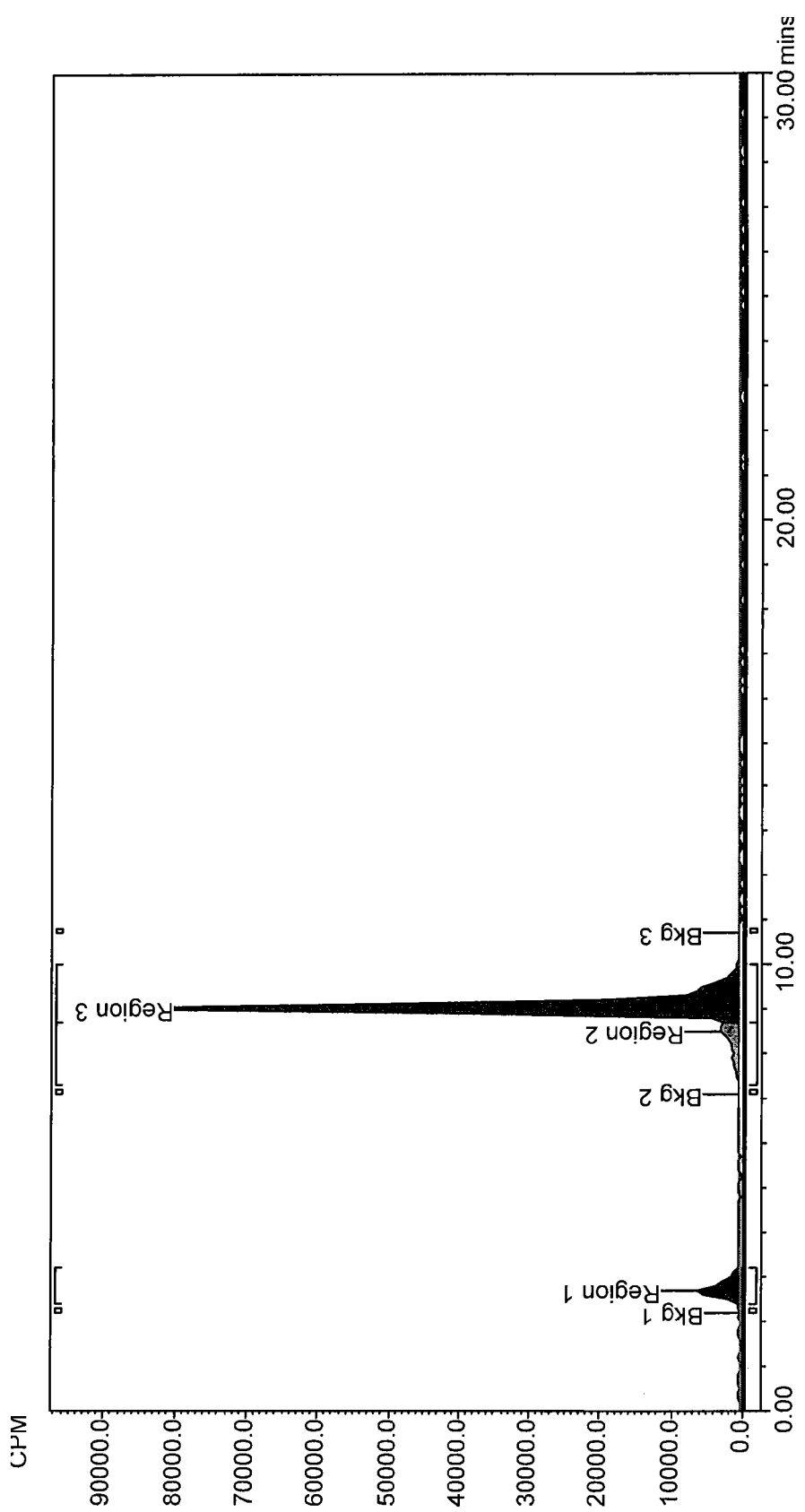
FIG. 2. F-18+excess IMP 272+AlCl$_3$ heated at 110° C. for 15 min, followed by analysis by reverse phase HPLC.
Figure 3:
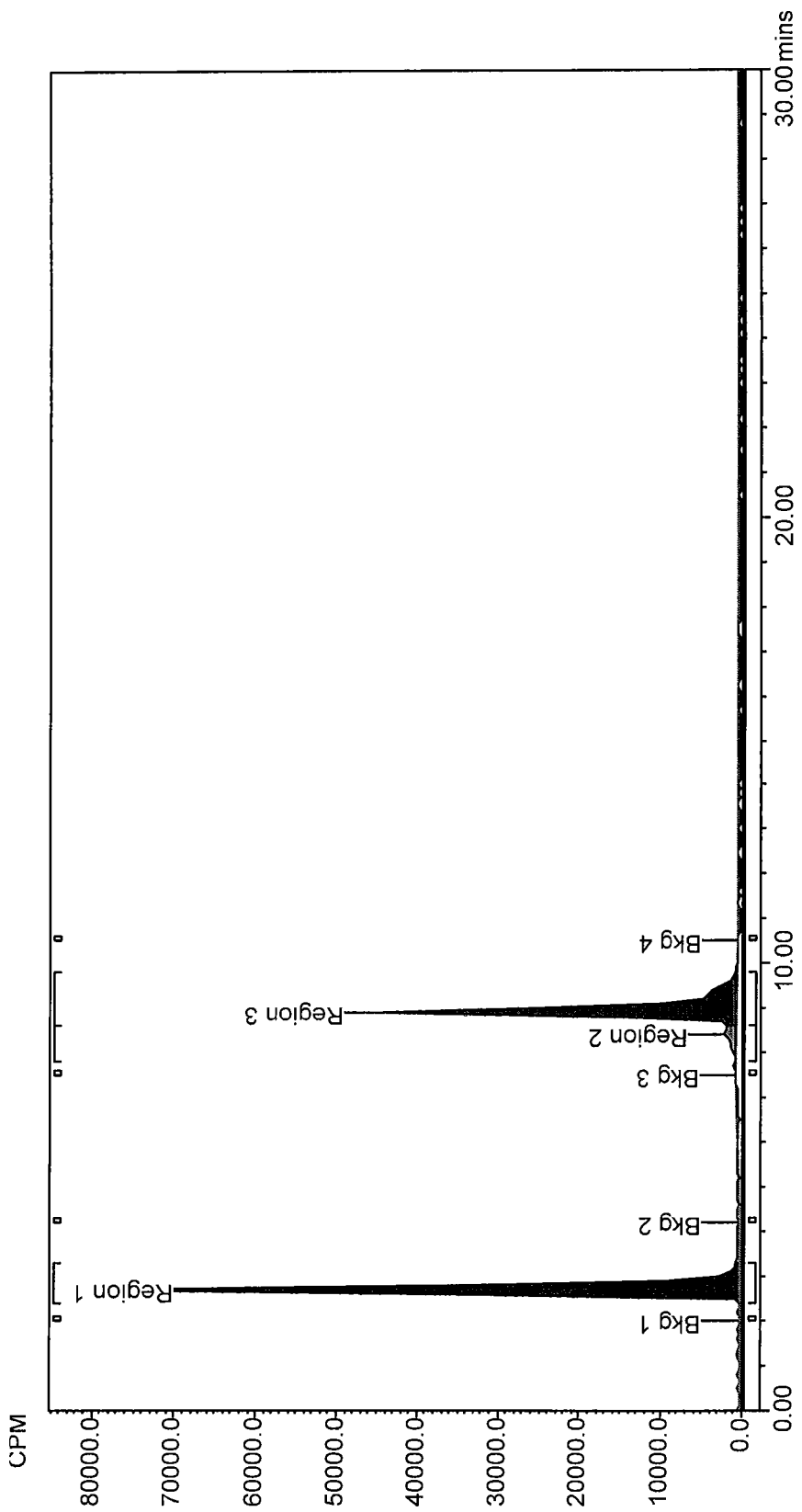
FIG. 3. Phosphate Challenge in PBS for 90 min at room temp. Aliquot of F-18+excess IMP 272+AlCl$_3$ heated at 110° C. for 15 min and analyzed by reverse phase HPLC.

F-18 Labeling of IMP 272—A 3 μL aliquot of the aluminum stock solution was placed in a REACTI-VIAL™ and mixed with 50 μL F-18 (as received) and 3 μL of the IMP 272 solution. The solution was heated in a heating block at 110° C. for 15 min and analyzed by reverse phase HPLC. The HPLC trace (FIG. 1) showed 93% free F-18 and 7% bound to the peptide. An additional 10 μL of the IMP 272 solution was added to the reaction and it was heated again and analyzed by reverse phase HPLC (FIG. 2). The HPLC trace showed 8% F-18 at the void volume and 92% of the activity attached to the peptide. The remainder of the peptide solution was incubated at room temperature with 150 μL PBS for ~1 hr and then examined by reverse phase HPLC. The HPLC (FIG. 3) showed 58% F-18 unbound and 42% still attached to the peptide. The data indicate that F-18-Al-DTPA complex may be unstable when mixed with phosphate.

Reverse Phase HPLC—Reverse phase HPLC analysis was done under the following conditions:
Column: WATERS® XTERRA™ MS C$_{18}$ 5 μm, 4.6×250 mm
Flow Rate: 1 mL/min
Gradient Buffers Buffer C, 0.1% NH$_4$OAc in DI water, Buffer D, 90% acetonitrile 10% water and 0.1% NH$_4$OAc
Gradient: 100% Buffer C to 100% Buffer D using a linear gradient over 30 min.
Run Time: 30 min
Size Exclusion HPLC—The size exclusion HPLC was done under the following conditions:
Column: BIORAD® BIO-SIL™ SEC 250, 300×7.8 mm
Gradient: Isocratic
Eluent Buffer: 0.2 M Phosphate pH 6.8
Flow Rate: 1 mL/min
Run Time: 30 min
All the traces shown in the Figures herein are radiometric traces using a PERKIN ELMER® 610Tr to monitor the emission of F-18. Tables 1-3 are tabular representations of the data shown in FIGS. 1-3 respectively.

TABLE 1

| | Regions: F-18 Detector: FSA | | | | | | |
|---|---|---|---|---|---|---|---|
| Name | Start (mins) | End (mins) | Retention (mins) | Height (CPM) | Area (CPM) | % ROI (%) | % Total (%) |
| Bkg 1 | 2.20 | 2.30 | 2.20 | 130.0 | | | |
| Region 1 | 2.30 | 3.30 | 2.60 | 85270.0 | 200050.0 | 93.15 | 96.31 |
| Bkg 2 | 4.40 | 4.50 | 4.40 | 210.0 | | | |
| Region 2 | 8.70 | 9.80 | 9.00 | 5590.0 | 14720.0 | 6.85 | 7.09 |
| 2 Peaks | | | | | 214770.0 | 100.00 | 103.40 |

TABLE 2

Regions: F-18 Detector: FSA

| Name | Start (mins) | End (mins) | Retention (mins) | Height (CPM) | Area (CPM) | % ROI (%) | % Total (%) |
|---|---|---|---|---|---|---|---|
| Bkg 1 | 2.20 | 2.30 | 2.20 | 340.0 | | | |
| Region 1 | 2.40 | 3.20 | 2.70 | 6450.0 | 20549.6 | 7.76 | 8.23 |
| Bkg 2 | 7.10 | 7.20 | 7.10 | 630.0 | | | |
| Region 2 | 7.30 | 8.70 | 8.50 | 3140.0 | 13113.6 | 4.95 | 5.25 |
| Region 3 | 8.70 | 10.00 | 9.00 | 93700.0 | 231023.9 | 87.28 | 92.57 |
| Bkg 3 | 10.70 | 10.80 | 10.70 | 520.0 | | | |
| 3 Peaks | | | | | 264687.1 | 100.00 | 106.06 |

TABLE 3

Regions: F-18 Detector: FSA

| Name | Start (mins) | End (mins) | Retention (mins) | Height (CPM) | Area (CPM) | % ROI (%) | % Total (%) |
|---|---|---|---|---|---|---|---|
| Bkg 1 | 2.00 | 2.10 | 2.00 | 350.0 | | | |
| Region 1 | 2.40 | 3.30 | 2.70 | 81930.0 | 162403.6 | 58.23 | 62.44 |
| Bkg 2 | 4.20 | 4.30 | 4.20 | 410.0 | | | |
| Bkg 3 | 7.50 | 7.60 | 7.50 | 780.0 | | | |
| Region 2 | 7.80 | 8.60 | 8.40 | 2110.0 | 5564.7 | 2.00 | 2.14 |
| Region 3 | 8.60 | 9.80 | 8.90 | 44590.0 | 110942.0 | 39.78 | 42.66 |
| Bkg 4 | 10.50 | 10.60 | 10.50 | 460.0 | | | |
| 3 Peaks | | | | | 278910.3 | 100.00 | 107.24 |

Figure 4:
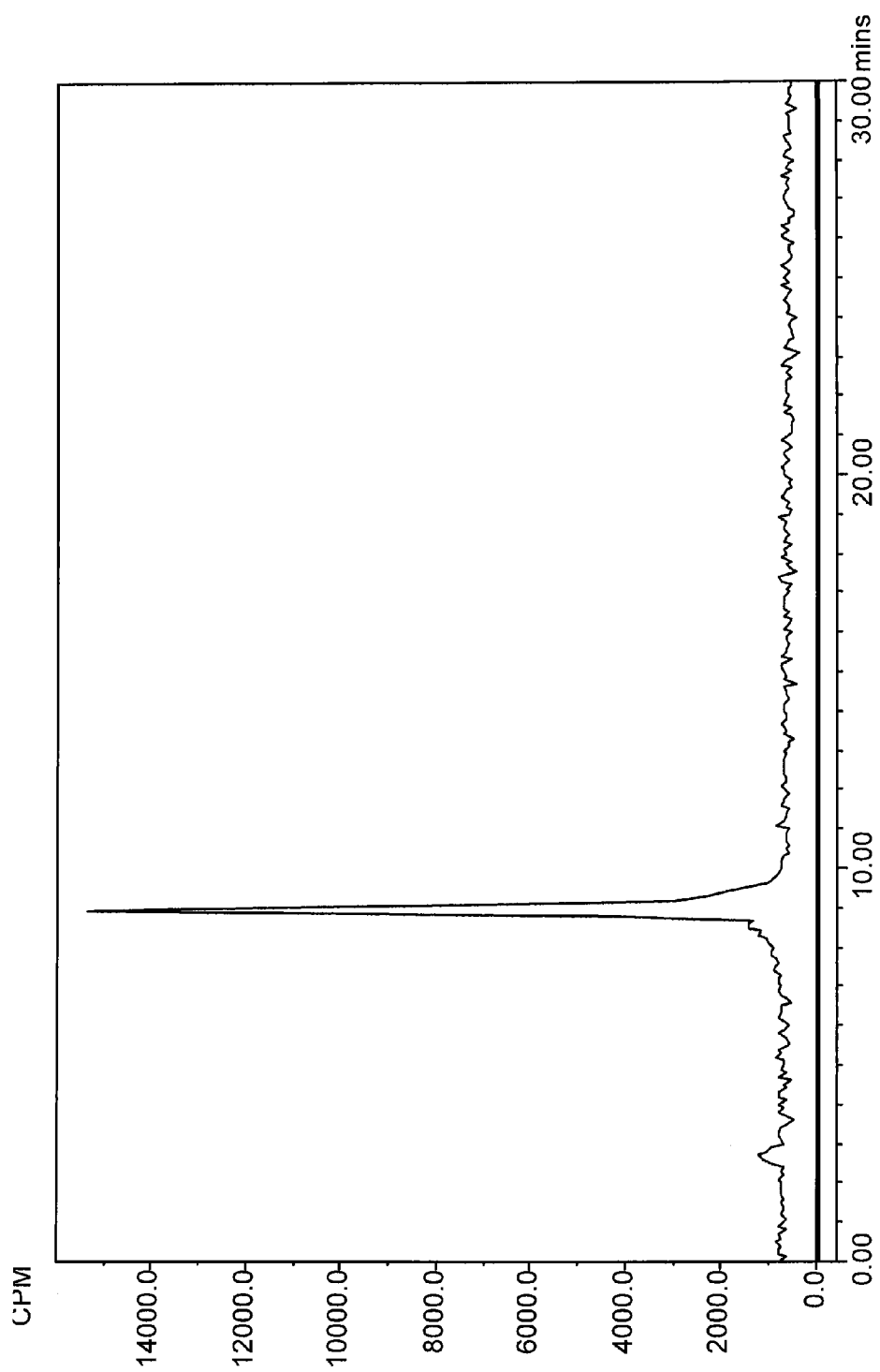
FIG. 4. Stability of Al-$^{18}$F IMP 272 in H$_2$O, reverse phase HPLC. F-18 Labeled IMP 272 just after HLB column purification.
Figure 5:
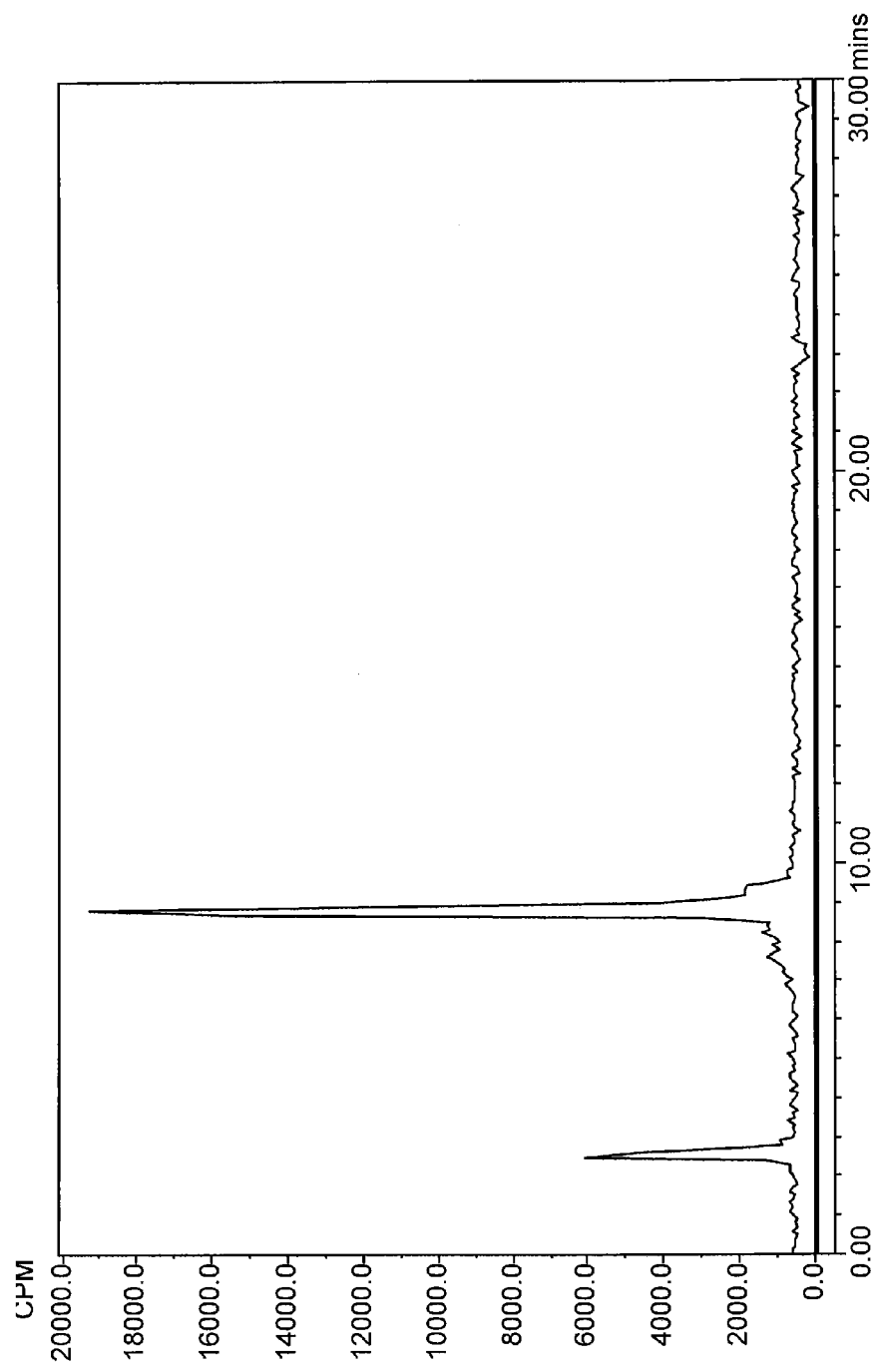
FIG. 5. Purified F-18 labeled IMP 272 after 40 min diluted in water at 25° C.
Figure 6:
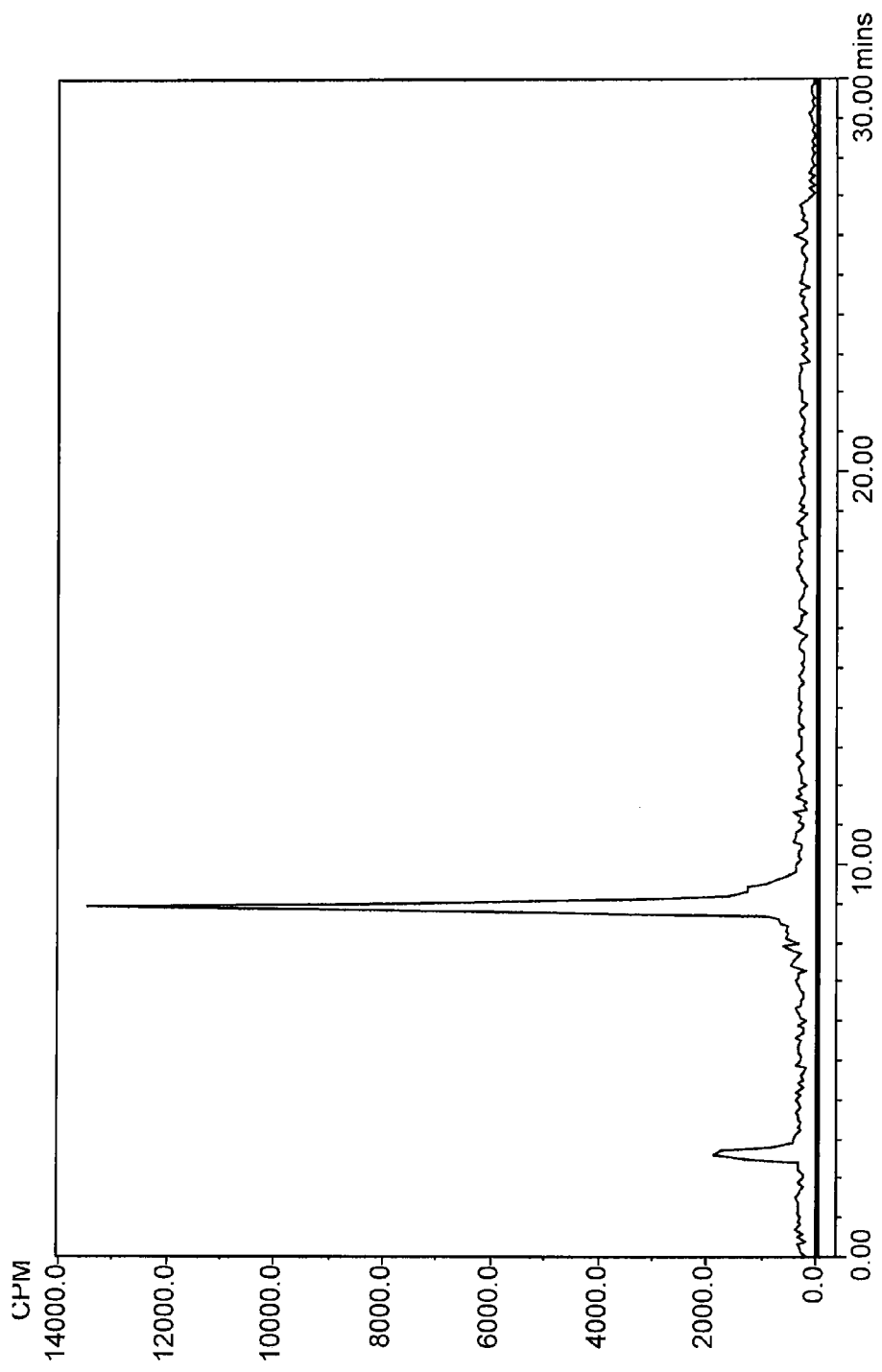
FIG. 6. Al-$^{18}$F IMP 272 crude reaction mixture reverse phase HPLC used for immunoreactivity study.
Figure 7:
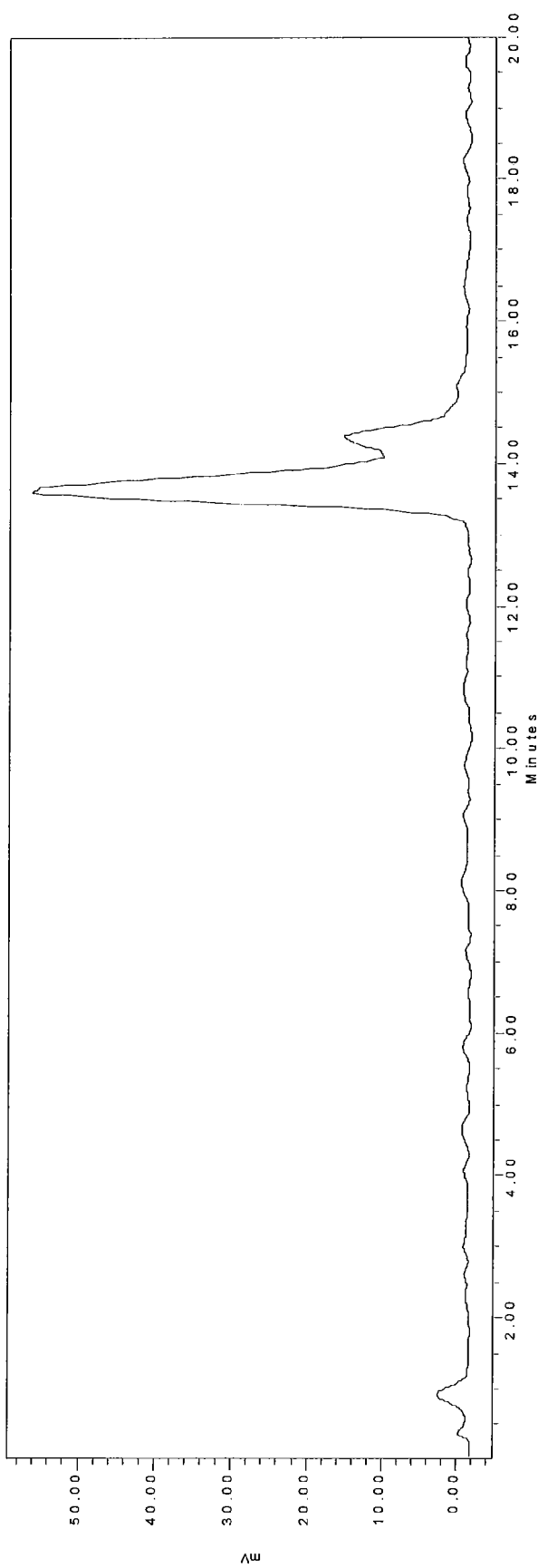
FIG. 7. Immunoreactivity of Al-$^{18}$F IMP 272, size exclusion HPLC, F-18 Al IMP 272 Crude Reaction Mixture SEC 79% Recovery.

The labeled peptide was purified by applying the labeled peptide solution onto a 1 cc (30 mg) WATERS® HLB column (Part # 186001879) and washing with 300 µL water to remove unbound F-18. The peptide was eluted by washing the column with 2×100 µL 1:1 MeOH/H$_2$O. The purified peptide was incubated in water at 25° C. and analyzed by reverse phase HPLC (FIG. 4, FIG. 5). The HPLC analysis showed that the F-18 labeled IMP 272 was not stable in water (FIG. 4, FIG. 5). Comparison of FIG. 4 and FIG. 5 shows that after a 40 min incubation in water about 17% of the F-18 was released from the peptide.

Example 2

Immunoreactivity of F-18 IMP 272

Figure 8:
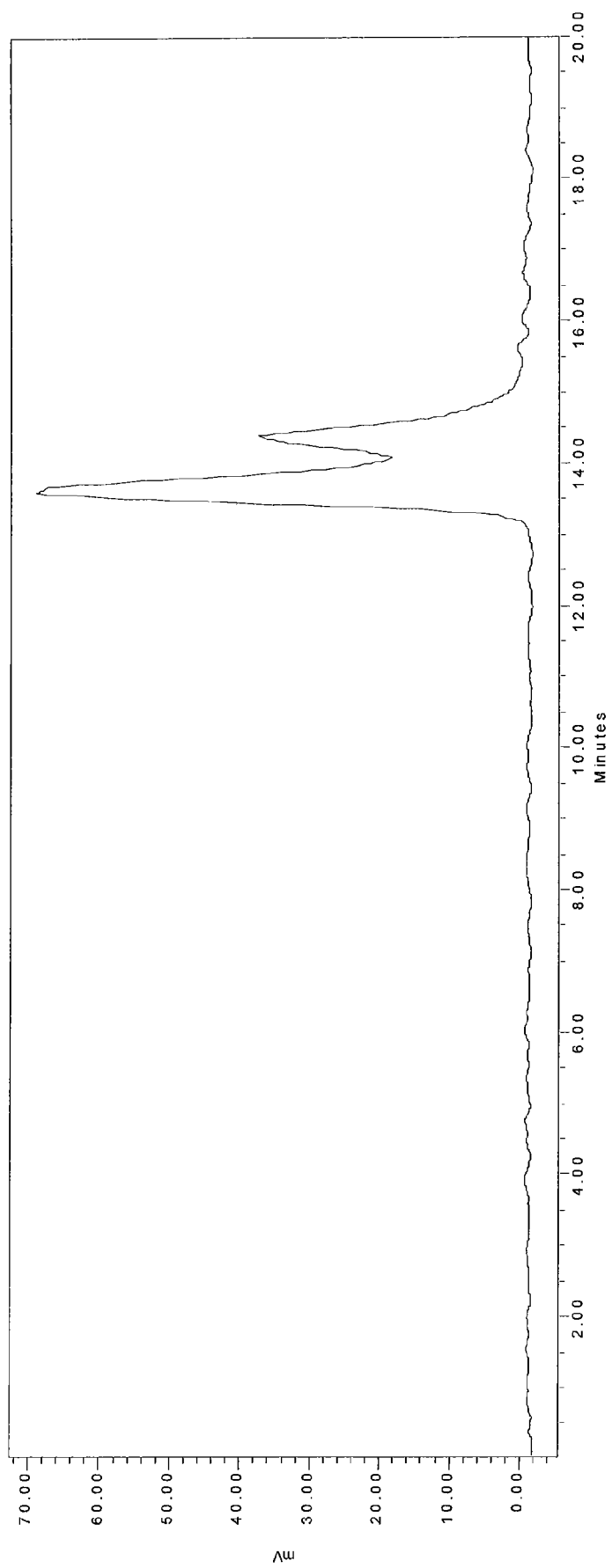
FIG. 8. F-18 Al IMP 272 Crude Reaction Mixture SEC+ hMN-14×734 81% Recovery
Figure 9:
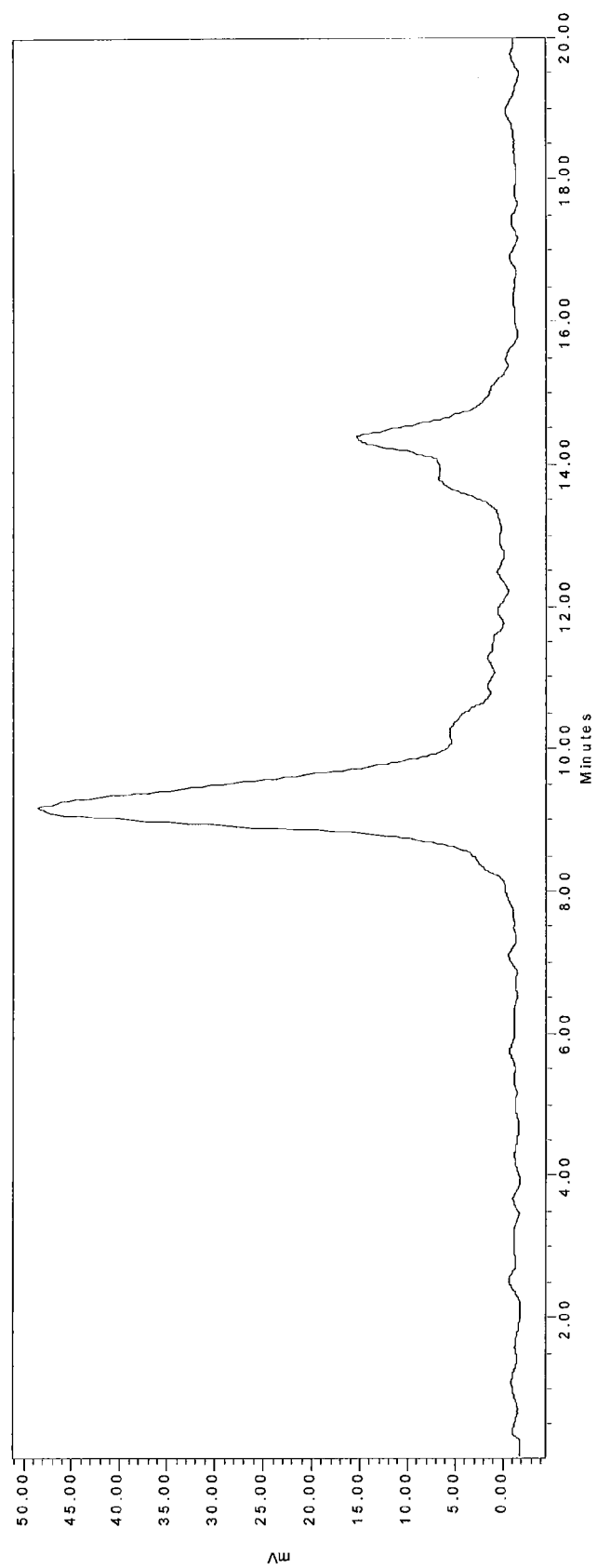
FIG. 9. F-18 Al IMP 272 Crude Reaction Mixture SEC+ hMN-14×679 78% Recovery

The peptide (16 µL 2 mM IMP 272, 48 µg) was labeled with F-18 and analyzed for antibody binding by size exclusion HPLC (radiometric traces, FIG. 6 to FIG. 9). The size exclusion HPLC showed that the peptide bound hMN-14×679 but did not bind to the irrelevant bispecific antibody hMN-14×734 (FIG. 8 vs. FIG. 9).

Example 3

IMP 272 F-18 Labeling with Other Metals

Figure 10:
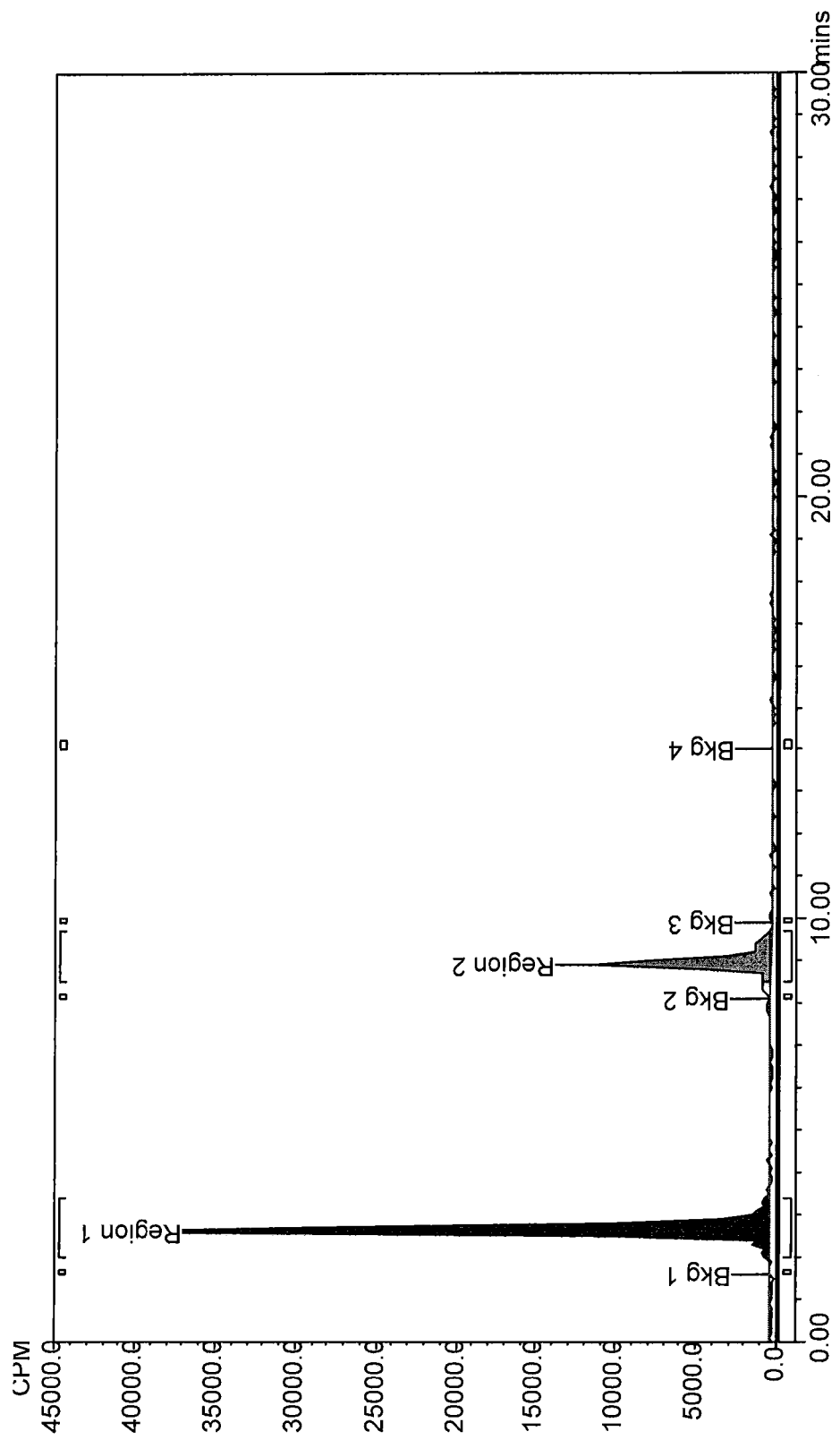
FIG. 10. Labeling of IMP 272 with F-18 Bound to Other Metals Reverse Phase HPLC. F-18 Labeling of IMP 272 with cold indium.
Figure 11:
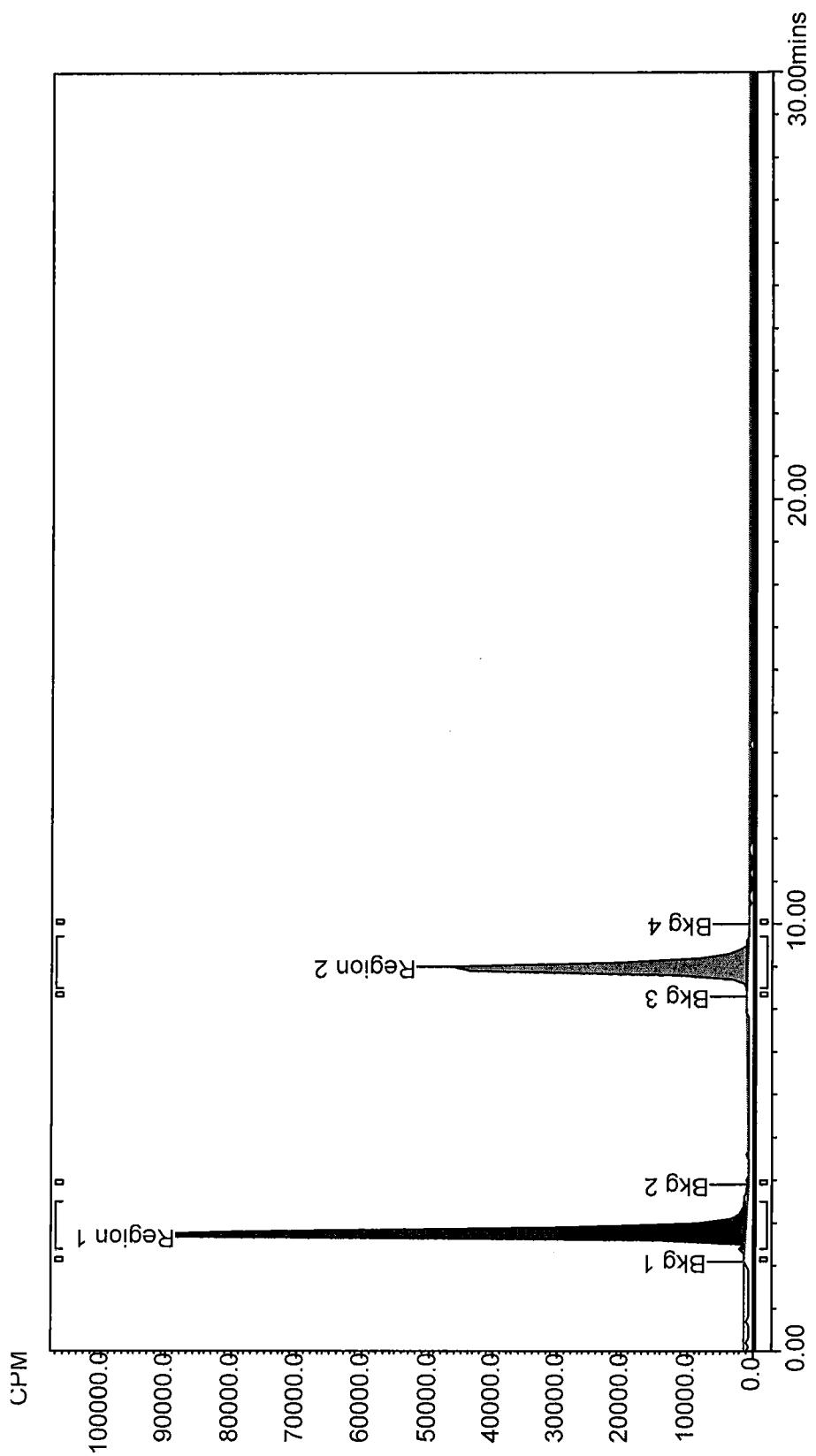
FIG. 11. F-18 Labeling of IMP 272 with cold gallium.
Figure 12:
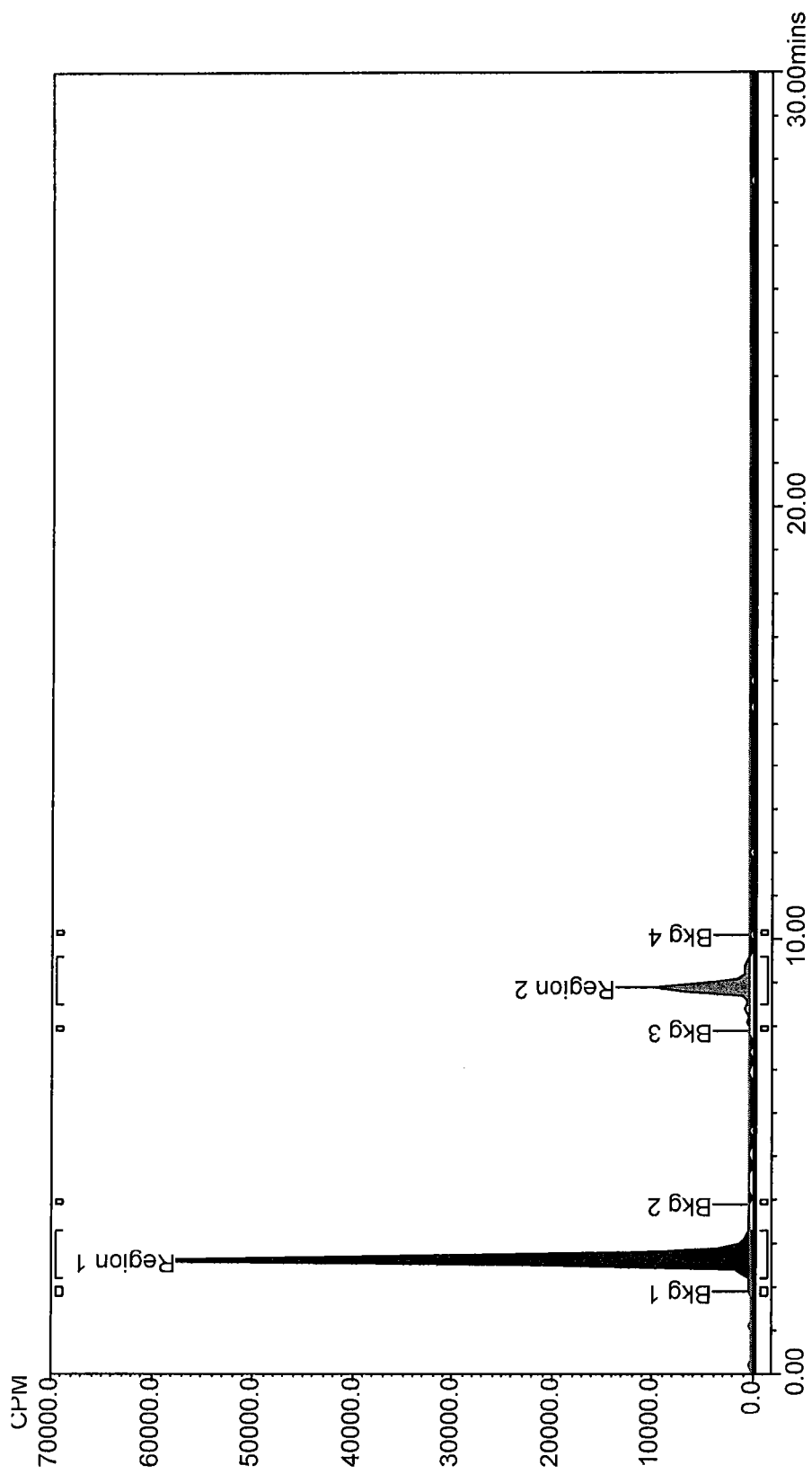
FIG. 12. F-18 Labeling of IMP 272 with cold zirconium.
Figure 13:
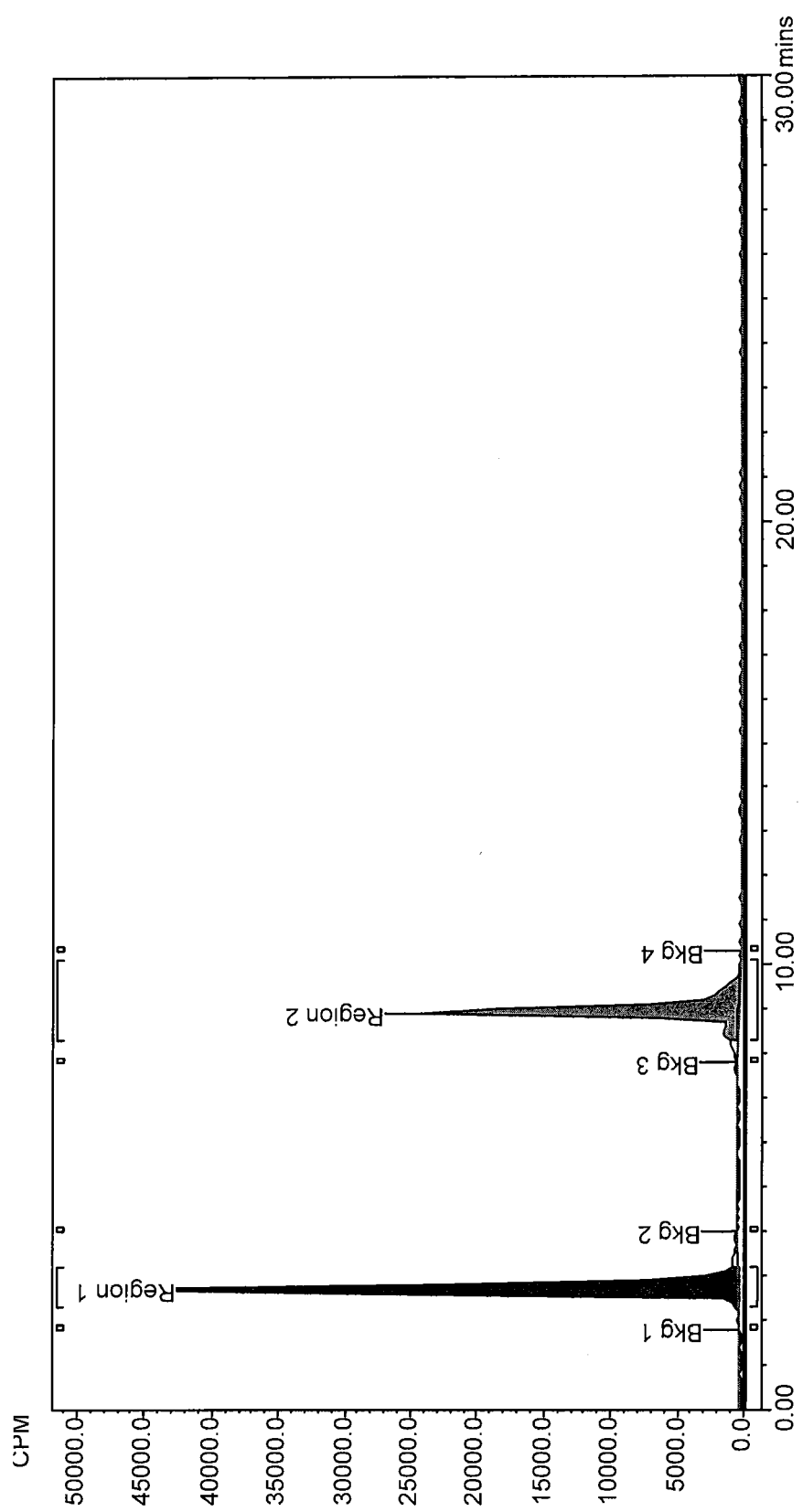
FIG. 13. F-18 Labeling of IMP 272 with cold lutetium.
Figure 14:
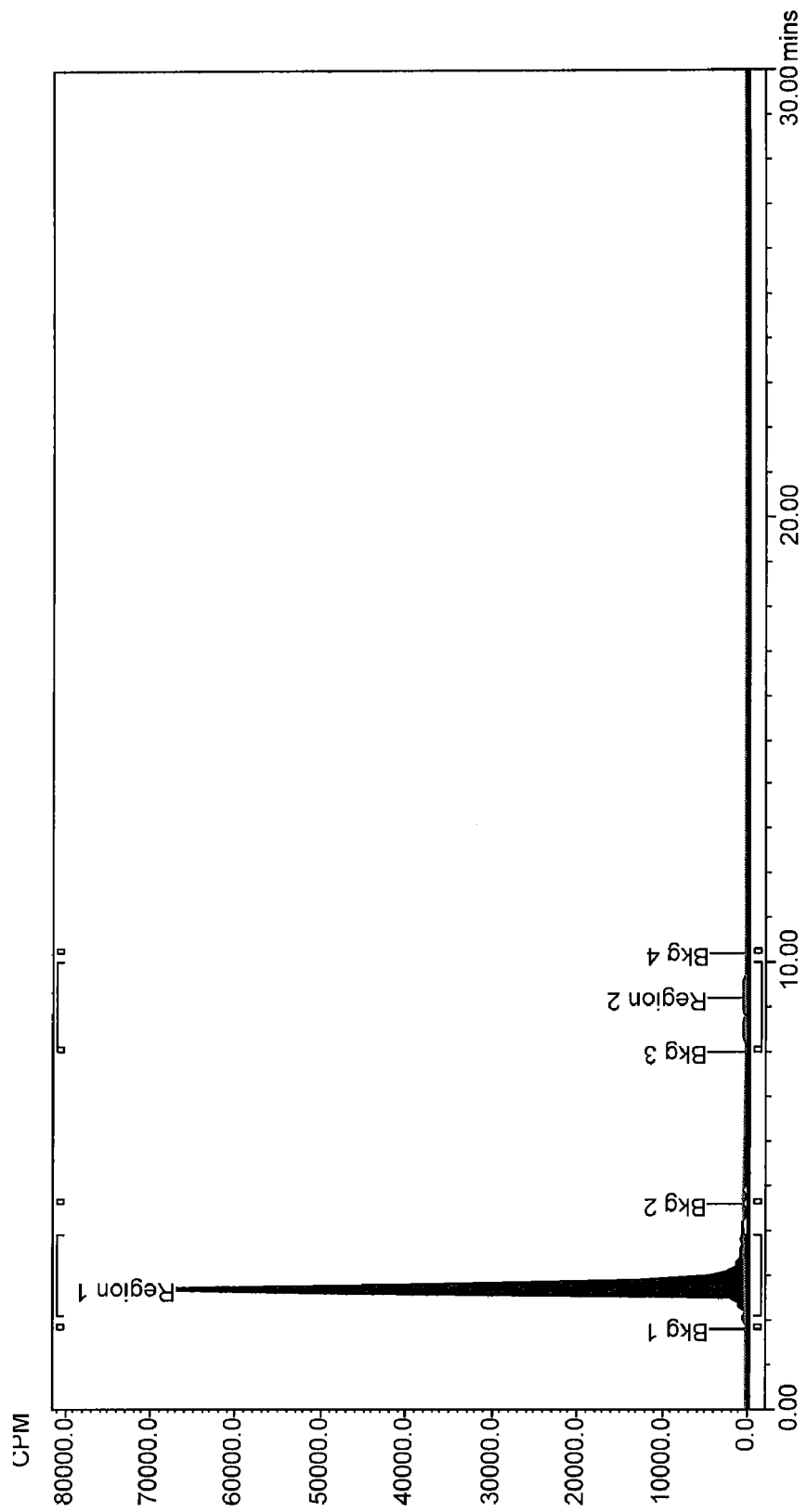
FIG. 14. F-18 Labeling of IMP 272 with cold yttrium.

A ~3 µL aliquot of the metal stock solution (6×10$^{-9}$ mol) was placed in a polypropylene cone vial and mixed with 75 µL F-18 (as received), incubated at room temperature for ~2 min and then mixed with 20 µL of a 2 mM (4×10$^{-8}$ mol) IMP 272 solution in 0.1 M NaOAc pH 4 buffer. The solution was heated in a heating block at 100° C. for 15 min and analyzed by reverse phase HPLC. The results are shown for labeling of IMP 272 with indium (FIG. 10), gallium (FIG. 11), zirconium (FIG. 12), lutetium (FIG. 13) and yttrium (FIG. 14).

Example 4

Standard F-18 Peptide Labeling Conditions Used to Screen Other Peptides For Al-$^{18}$F Binding A 3 µL aliquot of the 2 mM aluminum stock solution was placed in a polypropylene cone vial and mixed with 50 µL F-18 (as received), incubated at room temperature for ~2 min and then mixed with 16 to 20 µL of a 2 mM peptide solution in 0.1 M NaOAc pH 4 buffer. The solution was heated in a heating block at 100° C. for 15 min and analyzed by reverse phase HPLC (PHENOMENEX™, GEMINI®, 5µ, C-18, 110A, 250×4.6 mm HPLC Column).

Peptides Tested

IMP 272: DTPA-Gln-Ala-Lys(HSG)-D-Tyr-Lys(HSG)-NH$_2$ MH$^+$ 1512

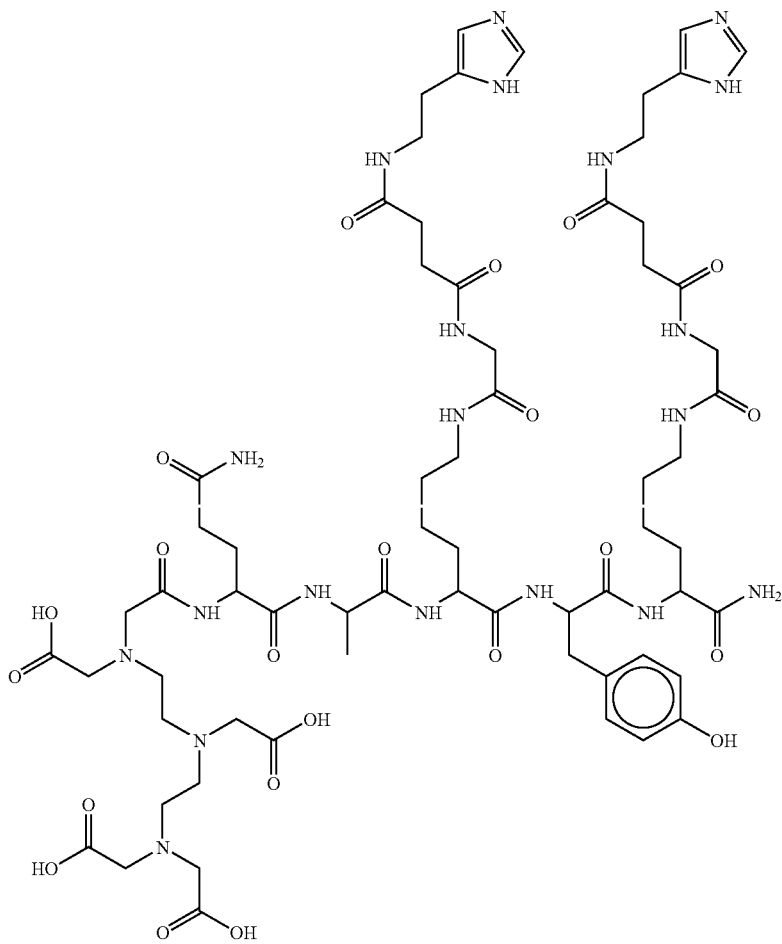
IMP 288 DOTA-D-Tyr-D-Lys(HSG)-D-Glu-D-Lys(HSG)-NH$_2$ MH$^+$ 1453
IMP 326 DTPA-ITC—NH—NH-Phe-CO-D-Tyr-D-Lys(HSG)-D-Glu-D-Lys(HSG)-NH$_2$ MH$^+$ 1477
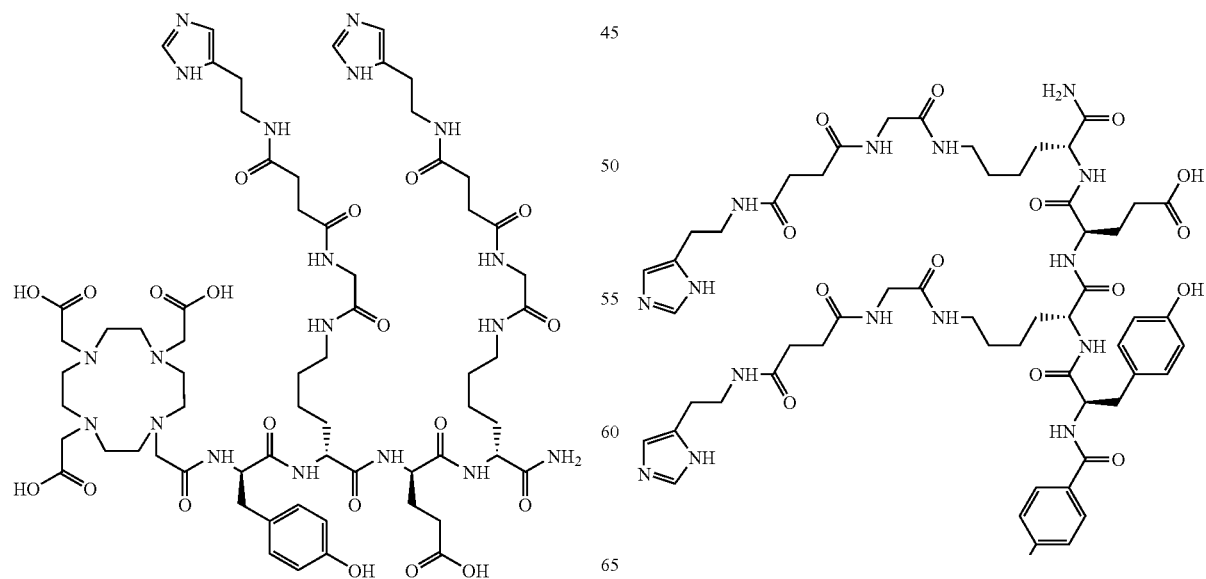

-continued
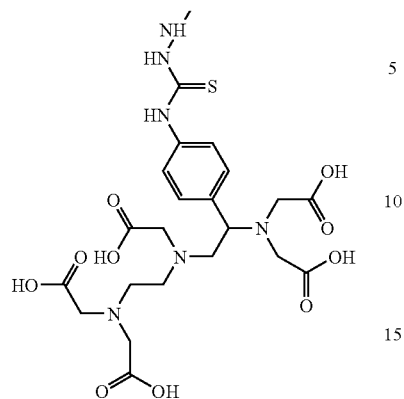
IMP 329 Deferoxamine-NH—CS—NH—NH-Ph-CO-D-Tyr-D-Lys(HSG)-D-Glu-D-Lys(HSG)-NH$_2$   MH$^+$   1804
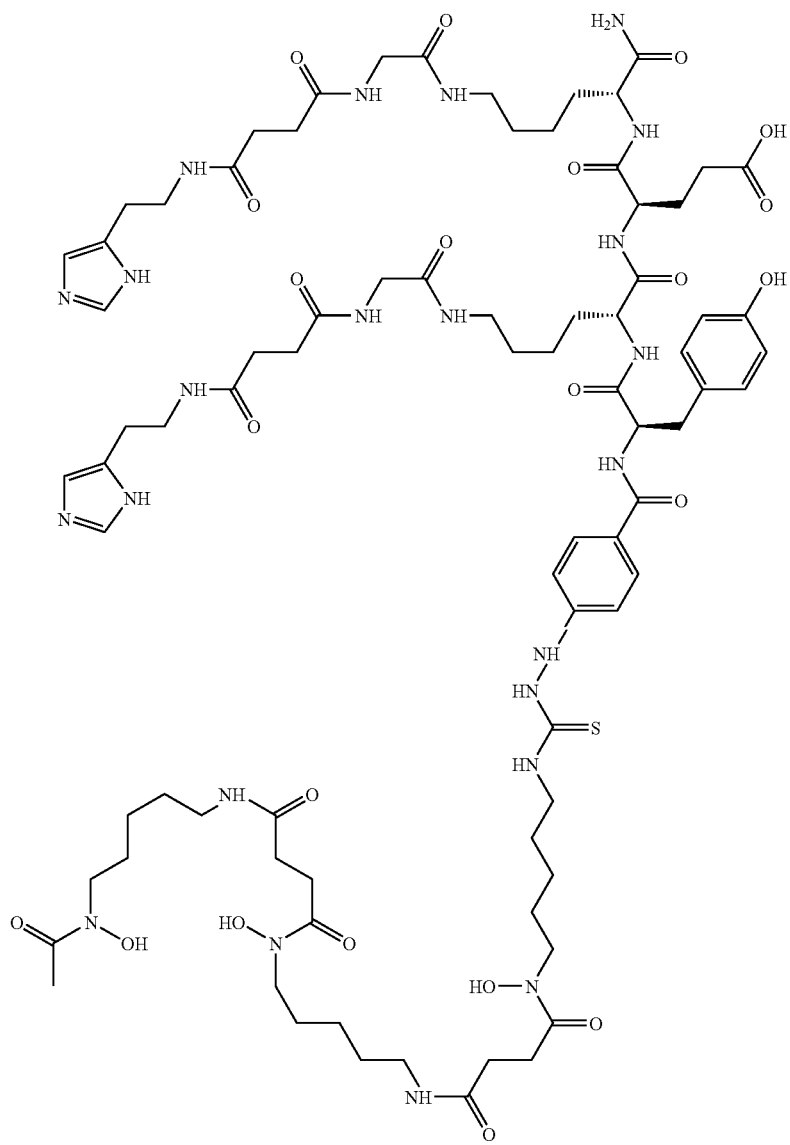

IMP 331 NTA-iAsp-D-Ala-D-Lys(HSG)-D-Tyr-D-Lys(HSG)-NH₂ MH⁺ 1240
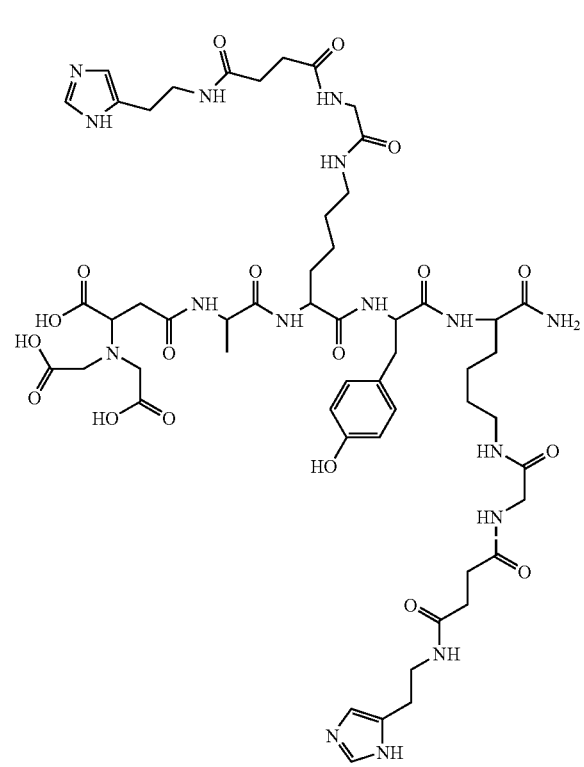
IMP 333 DTPA-Dpr(DTPA)-D-Ala-D-Lys(HSG)-D-Ala-D-Lys(HSG)-NH₂ MH⁺ 1845
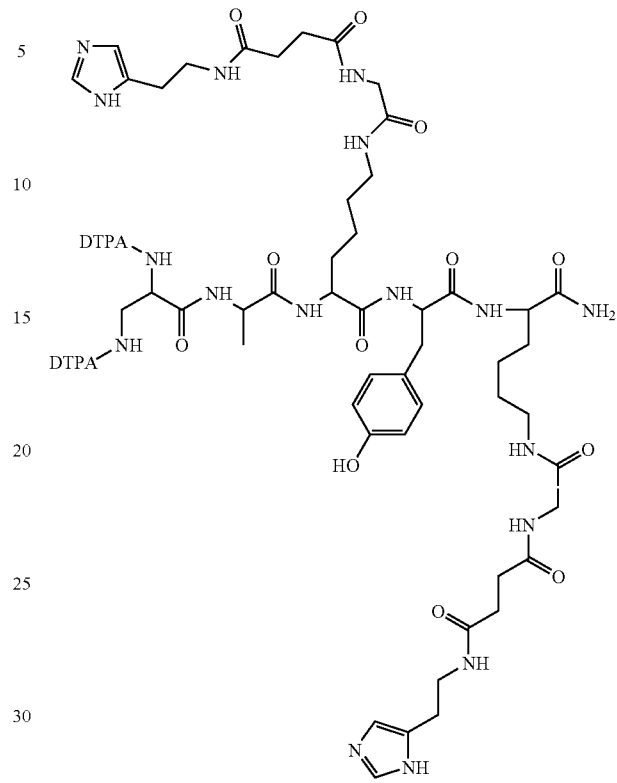
IMP 332 EDTADpr-D-Ala-D-Lys(HSG)-D-Ala-D-Lsy(HSG)-NH₂ MH⁺ 1327
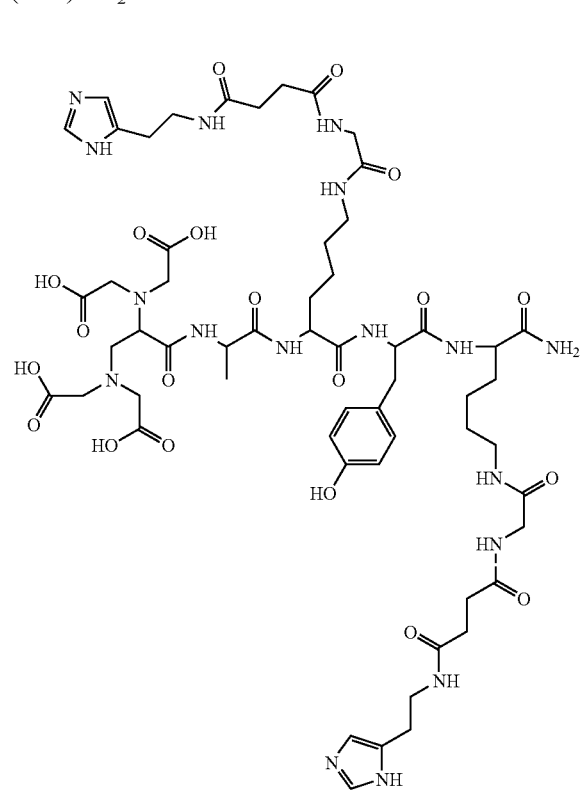
IMP 334 (H₂O₃P)₂—C(OH)—(CH2)₃—NH-Gly-D-Lys(HSG)-D-Glu-D-Lys(HSG)-NH₂ MH⁺ 1192
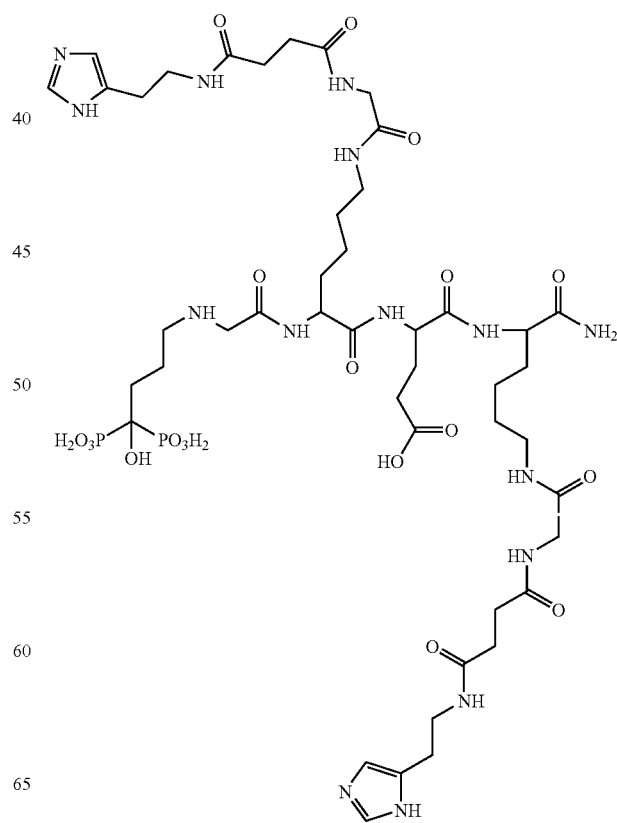

IMP 337 Ac-D-Ser(PO₃H₂)-D-Ser(PO₃H₂)-D-Ala-D-Lys(HSG)-D-Ala-D-Lys(HSG)-NH₂ MH⁺ 1291

IMP 338 Ac-D-Ser(PO₃H₂)-D-Ala-D-Lys(HSG)-D-Ala-D-Lys(HSG)-NH₂ MH⁺ 1126

IMP 345 DTPA-D-Ser(PO₃H₂)-D-Ala-D-Lys(HSG)-D-Ala-D-Lys(HSG)-NH₂ MH⁺ 1459

IMP 349 DTPA-D-Cys((H₂O₃P)₂—CH—CH₂—S)-D-Ala-D-Lys(HSG)-D-Ala-D-Lys(HSG)-NH₂ MH⁺ 1583

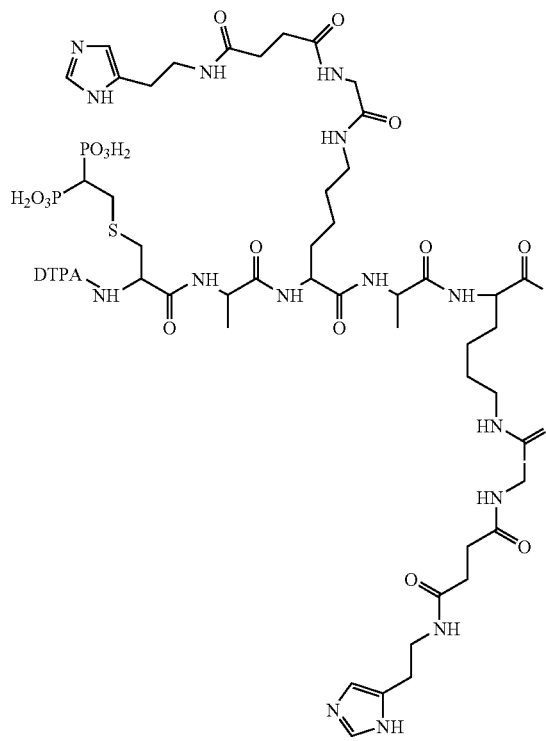

IMP 361 DTPA-Dpr(BrCH₂CO—)-D-Ala-D-Lys(HSG)-D-Ala-D-Lys(HSG)-NH₂ MH⁺ 1498

IMP 366 DTPA-Dpr(Ph-S—CH₂CO—)-D-Ala-D-Lys(HSG)-D-Ala-D-Lys(HSG)-NH₂ MH⁺ 1528

IMP 368 Sym-DTPA-D-Ala-D-Lys(HSG)-D-Ala-D-Lys(HSG)-NH₂ MH⁺ 1292

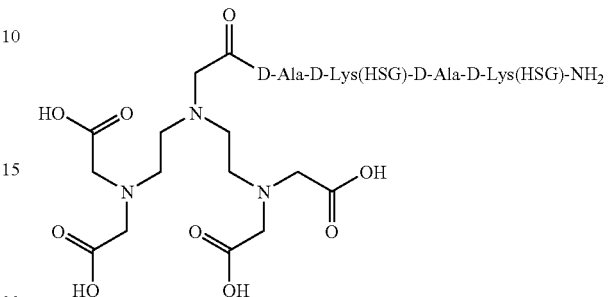

IMP 369 Sym-DTPA-NH—CH(2-Br-Phe-)—CH₂—CO-D-Ala-D-Lys(HSG)-D-Ala-D-Lys(HSG)-NH₂ MH⁺ 1517

IMP 370 Sym-DTPA-NH—CH(2-O₂N-Phe-)—CH₂—CO-D-Ala-D-Lys(HSG)-D-Ala-D-Lys(HSG)-NH₂ MH⁺ 1484

IMP 371 DTPA-NH—CH(2-O₂N-Phe-)—CH₂—CO-D-Ala-D-Lys(HSG)-D-Ala-D-Lys(HSG)-NH₂ MH⁺ 1484

IMP 372 DTPA-Dpr(Ser)-D-Ala-D-Lys(HSG)-D-Ala-D-Lys(HSG)-NH₂ MH⁺ 1465

IMP 373 DTPA-Dpr(Sym-DTPA)-D-Ala-D-Lys(HSG)-D-Ala-D-Lys(HSG)-NH₂ MH⁺ 1753

IMP 374 DTPA-Dpr(Cl—CH2CO-Cys(Et)-)-D-Ala-D-Lys(HSG)-D-Ala-D-Lys(HSG)—NH₂ MH⁺ 1585

IMP 375 DTPA-Dpr(2-Br-Phe-CHNH₂—CH₂—CO—)-D-Ala-D-Lys(HSG)-D-Ala-D-Lys(HSG)-NH₂ MH⁺ 1603

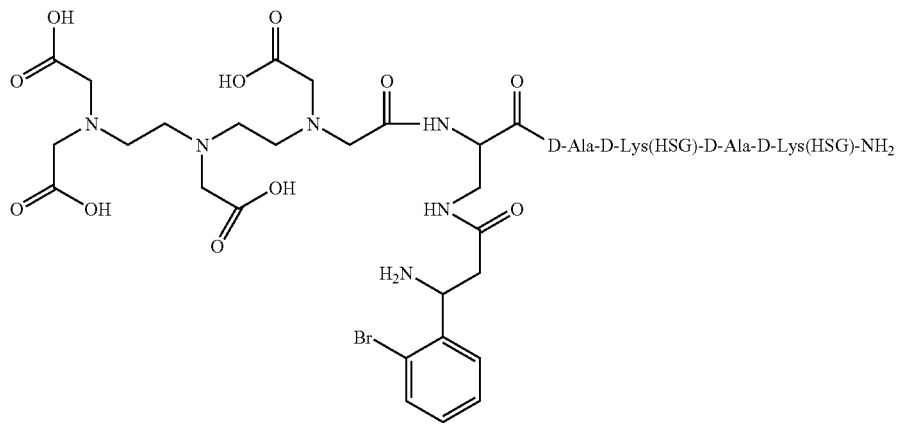

IMP 376 DTPA-Cys(HO₃S—S)-D-Tyr-D-Ala-D-Lys(HSG)-D-Ala-D-Lys(HSG)-NH₂ MH⁺ 1558

IMP 379 DTPA-Dpr(2-H₂N-Phe-CO—)-D-Ala-D-Lys(HSG)-D-Ala-D-Lys(HSG)-NH₂ MH⁺ 1497

IMP 382 DTPA-Dpr(H)-D-Ala-D-Lys(HSG)-D-Ala-D-Lys(HSG)-NH₂ MH⁺ 1378

IMP 383 DTPA-Dpr(Gla-)-D-Ala-D-Lys(HSG)-D-Ala-D-Lys(HSG)-NH₂ MH⁺ 1507

IMP 384 DTPA-Dpr(2-HO-Phe-CHNH₂—CH₂—CO—)-D-Ala-D-Lys(HSG)-D-Ala-D-Lys(HSG)-NH₂ MH⁺ 1541

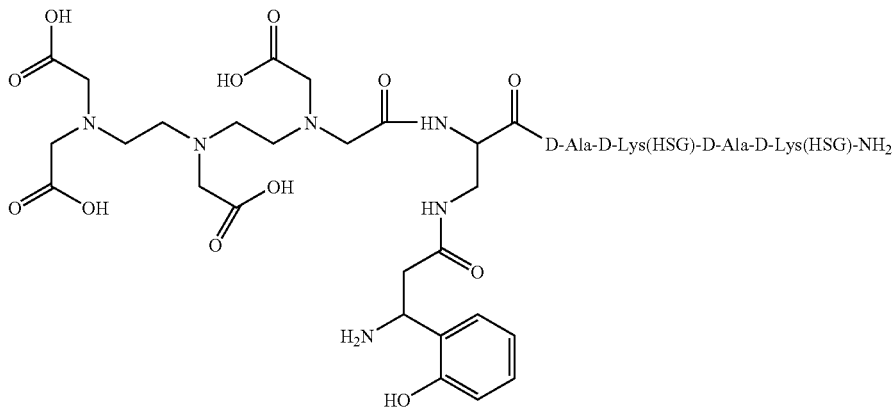
IMP 385 DTPA-Dpr(Dpr)-D-Ala-D-Lys(HSG)-D-Ala-D-Lys(HSG)-NH$_2$ MH$^+$ 1464
IMP 386 DTPA-Dpr(2-pyridyl-CH$_2$—CHNH$_2$—CO—)-D-Ala-D-Lys(HSG)-D-Ala-D-Lys(HSG)-NH$_2$ MH$^+$ 1526
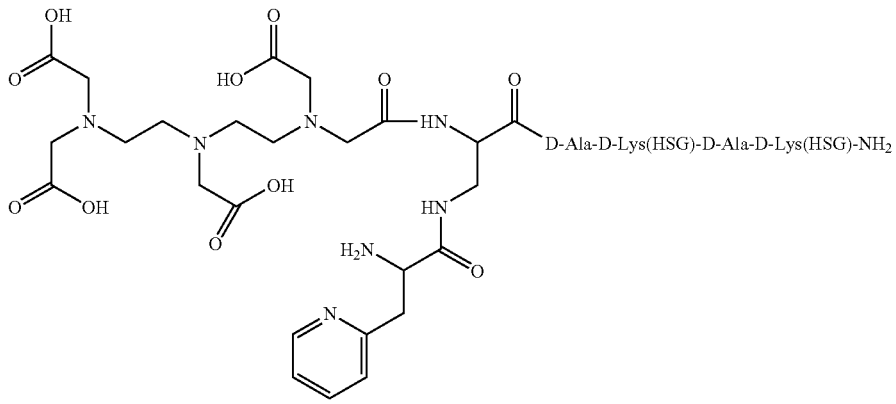
IMP 387 DTPA-Dpr(D-9-anthrylalanine)-D-Ala-D-Lys(HSG)-D-Ala-D-Lys(HSG)-NH$_2$ MH$^+$ 1625
IMP 389 DTPA-Dpr(2-carboxy piperizinyl)-D-Ala-D-Lys(HSG)-D-Ala-D-Lys(HSG)—NH$_2$ MH$^+$ 1490
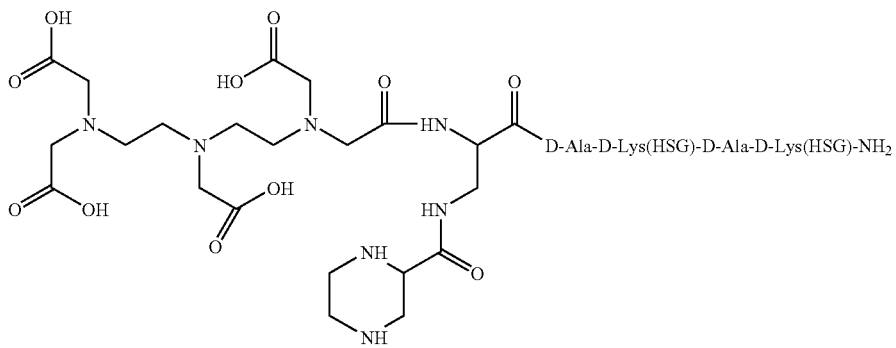

Results of Peptide Labeling Screening Study

Figure 15:
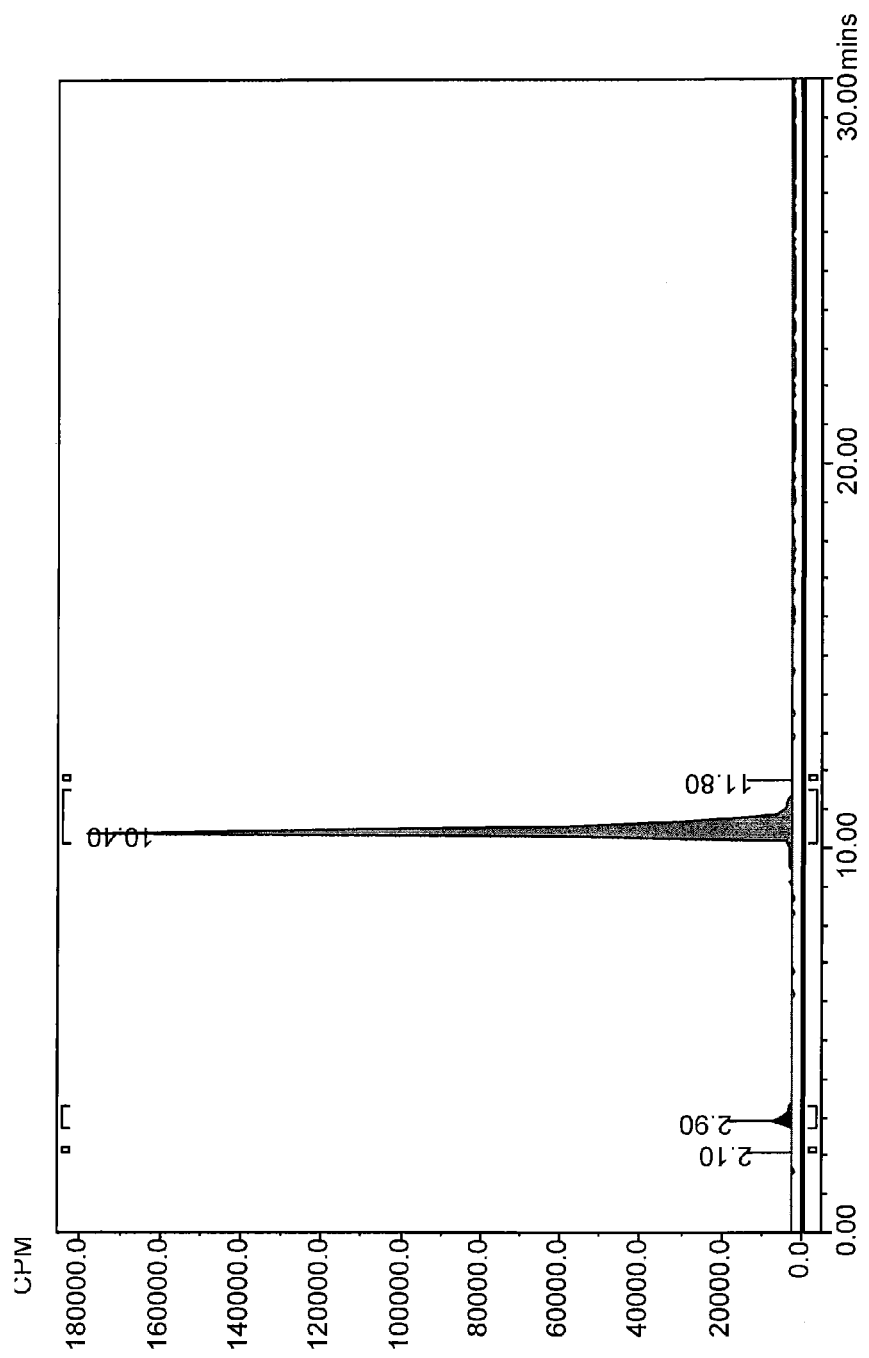
FIG. 15. Stability of Al-$^{18}$F IMP 375 in water, reverse phase HPLC. F-18 IMP 375 in water, crude labeled peptide (97.5%).
Figure 16:
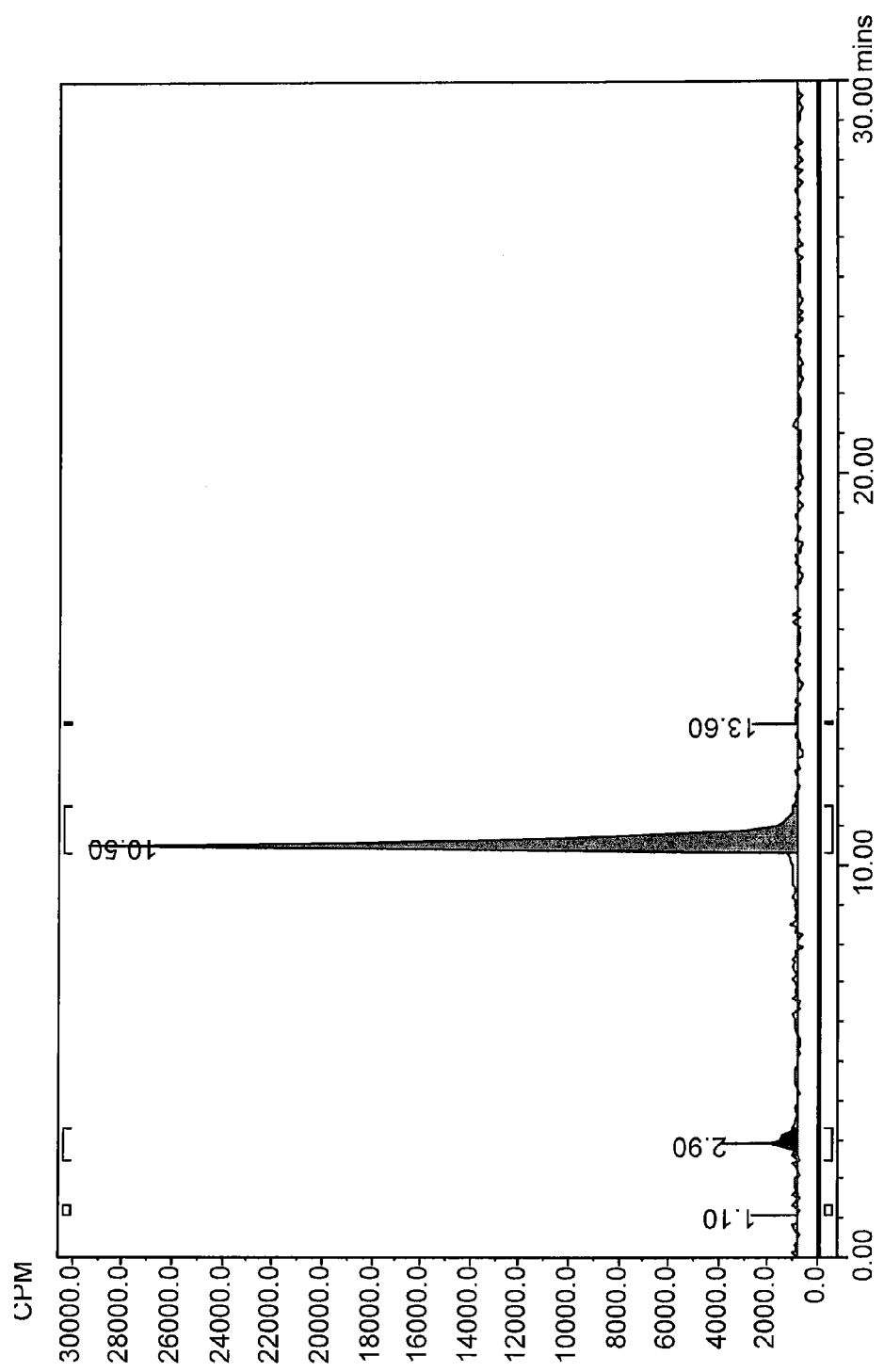
FIG. 16. F-18 IMP 375 In Water After 5 hr at 25° C. (95.4%)
Figure 17:
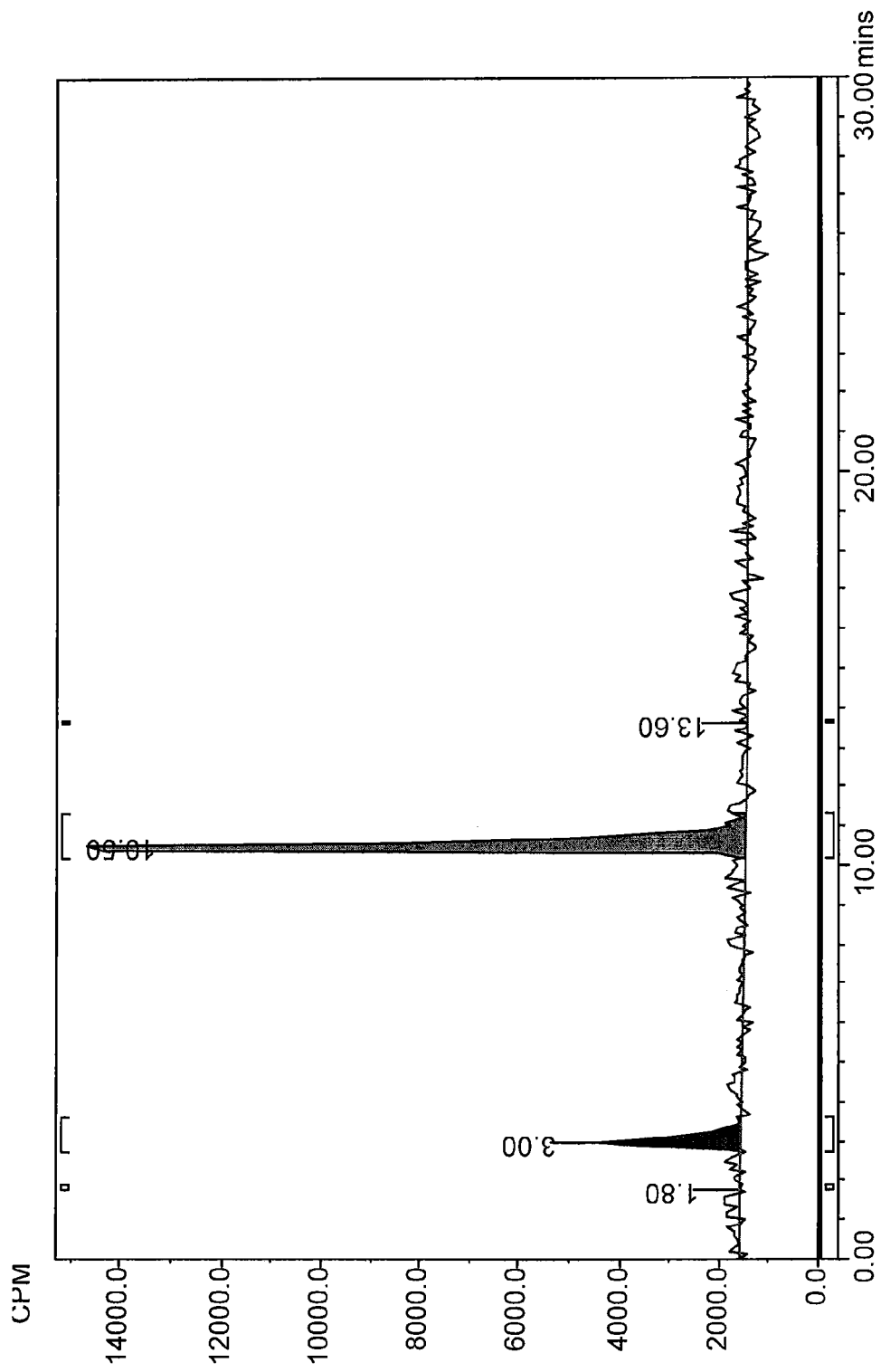
FIG. 17. Stability of Al-$^{18}$F IMP 375 in human serum 25° C., reverse phase HPLC. F-18 IMP 375 in human serum ~4.5 min (83.5%).
Figure 18:
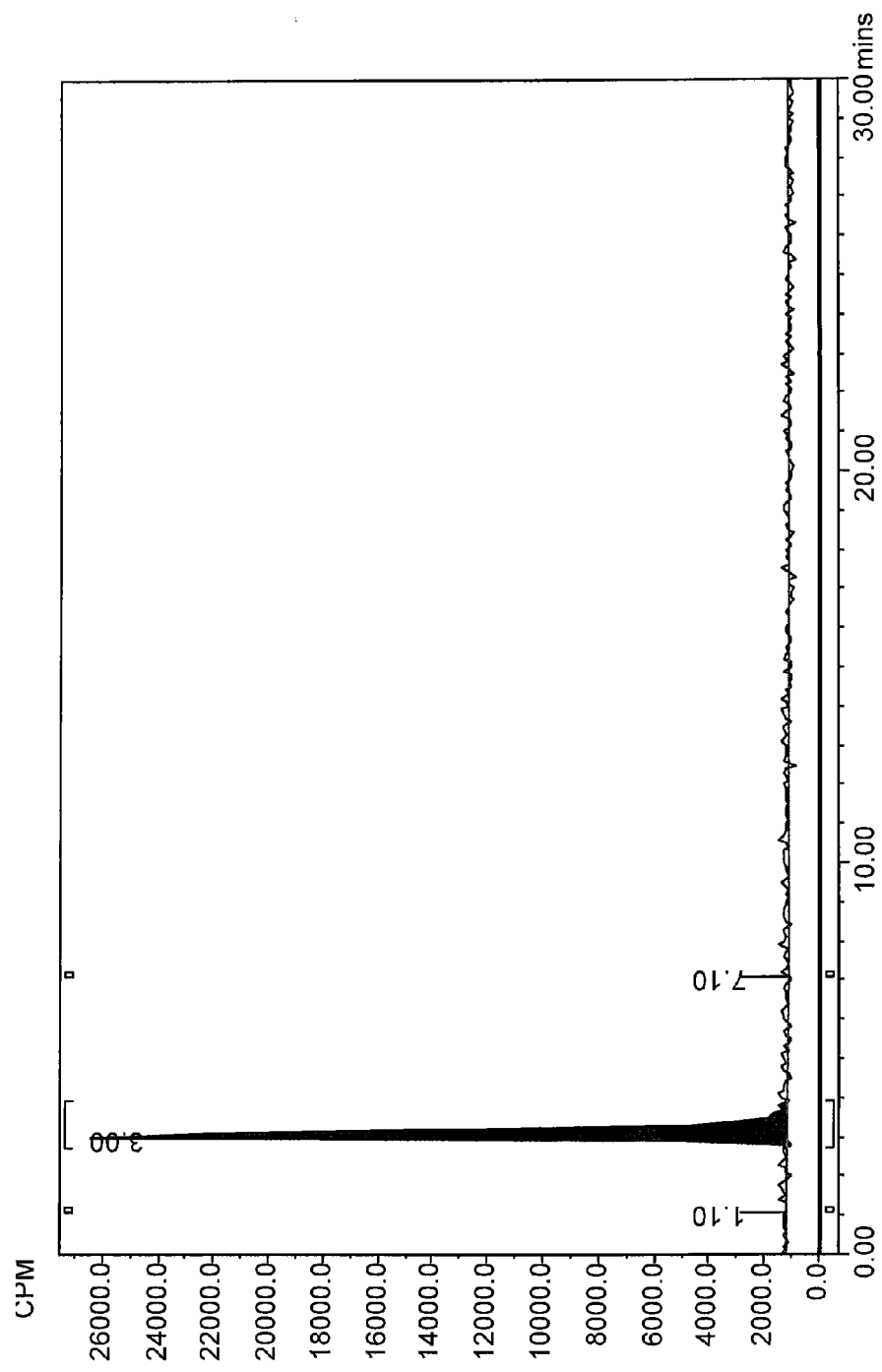
FIG. 18. F-18 IMP 375 In Human Serum 1.5 hr (0%)
FIG. 19A-19D. Stability of F-18 labeled IMP 449 in human serum at zero time (A) and after one hour (B), two hours (C), and four hours (D) of incubation.

Most of the DTPA derivatives showed labeling comparable to the labeling of IMP 272. There were exceptions, IMP 349, bearing the bisphosphonate group on a cysteine side chain, labeled very poorly. The DOTA ligand did not bind the Al-$^{18}$F. The ITC DTPA ligand of IMP 326 did not bind the Al-$^{18}$F as well as DTPA. The NTA ligand of IMP 331 did not bind the Al-$^{18}$F. The EDTA ligand of IMP 332 bound the Al-$^{18}$F but not as well as the DTPA. Symmetrical DTPA ligand did not bind the Al-$^{18}$F. The phosphonates and phosphate groups tested did not bind Al-$^{18}$F well under the conditions tested. The screen did show that a group that was attached near the DTPA could influence the stability of the Al-$^{18}$F-DTPA complex. The screen showed that IMP 375 labeled better and formed a complex that was significantly more stable than IMP 272. IMP 375 labeled well and was stable in water (FIG. 15, FIG. 16) but serum stability should be improved for in-vivo use (FIG. 17, FIG. 18).

The peptide labeling screening study only looked at the binding of Al-$^{18}$F. Some of the peptides that did not label well with Al-$^{18}$F might label better with another metal binding to the F-18.

Peptide Synthesis

The peptides were synthesized by solid phase peptide synthesis using the Fmoc strategy. Groups were added to the side chains of diamino amino acids by using Fmoc/Aloc protecting groups to allow differential deprotection. The Aloc groups were removed by the method of Dangles et. al. (*J. Org. Chem.* 1987, 52:4984-4993) except that piperidine was added in a 1:1 ratio to the acetic acid used. The unsymmetrical tetra-t-butyl DTPA was made as described in McBride et al. (US Patent Application Pub. No. US 2005/0002945 A1, application Ser. No. 10/776,470, Pub. Date. Jan. 6, 2005). The tri-t-butyl DOTA, symmetrical tetra-t-butyl DTPA and ITC-benzyl DTPA were obtained from MACROCYCLICS®. The Aloc/Fmoc Lysine and Dap (diaminopropionic acid derivatives (also Dpr)) were obtained from CREOSALUS® or BACHEM®. The Sieber Amide resin was obtained from NOVABIOCHEM®. The remaining Fmoc amino acids were obtained from CREOSALUS®, BACHEM®, PEPTECH® or NOVABIOCHEM®.

IMP 272 was synthesized as described (McBride et al., US Patent Application Publ. No. 20040241158 A1, application Ser. No. 10/768,707, Dec. 2, 2004). IMP 288 was made as described (McBride et al., *J. Nucl. Med.* 2006, 47:1678-1688).

IMP 326 The hydrazine peptide (IMP 319) was made on Sieber amide resin using Fmoc-D-Lys(Aloc)-OH, Fmoc-D-Glu(OBut)-OH, Fmoc-D-Lys(Aloc)-OH, Fmoc-D-Tyr(But)-OH and 4-(Boc-NH—NH—)C$_6$H$_4$—CO$_2$H in that order. The 4-(Boc-NH—NH—)C$_6$H$_4$—CO$_2$H was made by adding Boc dicarbonate to 4-hydrazinobenzoic acid in a dioxane sodium hydroxide solution.

After the addition of the Boc-hydrazide the side chain Aloc groups were removed and the Trityl-HSG-OH groups were added to the side chains of the lysines. The peptide was then cleaved from the resin with TFA and purified by HPLC to obtain the desired hydrazine bis-HSG peptide IMP 319 (MH$^+$ 1201). The hydrazide peptide (0.0914 g) was then mixed with 0.0650 g of ITC-Benzyl DTPA in 3 mL of 0.1 M sodium phosphate pH 8.2. The pH of the solution was adjusted with 1 M NaOH to keep the pH at pH 8.2. After the reaction between the peptide and the ITC-Benzyl DTPA was complete the peptide conjugate was purified by HPLC.

IMP 329 The deferoxamine isothiocyanate was prepared by mixing 1.0422 g of deferoxamine mesylate (1.59×10$^{-3}$ mol) with 0.2835 g (1.59×10$^{-3}$ mol) of thiocarbonyldiimidazole in 10 mL of 1:1 methanol/water. Triethylamine, 0.23 mL was added and the reaction was purified by reverse phase HPLC after 2.5 hr to obtain the deferoxamine isothiocyanate MNa$^+$ 625.

The hydrazine peptide, IMP 319, (0.0533 g, 4.4×10$^{-5}$ mol, MH$^+$ 1201) was mixed with 0.0291 g of deferoxamine isothiocyanate in a sodium phosphate buffer at pH 8.1 for two hours then purified by HPLC to afford the desired product MH+ 1804.

IMP 331 The following amino acids were attached to Sieber amide resin (0.58 mmol/g) Sieber amide resin in the order shown; Fmoc-D-Lys(Aloc)-OH, Fmoc-D-Tyr(But)-OH and Fmoc-D-Lys(Aloc)-OH. The Aloc groups were removed and Trt-HSG-OH was added to the side chains of the lysines. The Fmoc was removed, then Fmoc-D-Ala-OH and Fmoc-Asp-OBut were added in that order (0.5 g of resin). The Fmoc was removed and the nitrogen of the Asp was alkylated overnight with 3 mL t-butyl bromoacetate and 3.6 mL diisopropylethylamine in 3.4 mL of NMP. The peptide was cleaved from the resin with TFA and purified by reverse phase HPLC to obtain the desired peptide MH$^+$ 1240.

IMP 332 The peptide was made on 3 g of Sieber amide resin (0.58 mmol/g). The following amino acids were added to the resin in the order shown: Fmoc-D-Lys(Aloc)-OH, Fmoc-D-Tyr(But)-OH, Fmoc-D-Lys(Aloc)-OH, Fmoc-D-Ala-OH, and Fmoc-Dpr(Fmoc)-OH. The resin was split into portions for subsequent syntheses. One gram of the resin was removed and the Fmoc groups were removed from the diaminopropionic acid. The peptide was alkylated overnight with 3 mL t-butyl bromoacetate, 3.6 mL diisopropylethyl amine and 3.4 mL NMP. The side chain Aloc groups were then removed and the Trt-HSG-OH groups were added. The peptide was then cleaved from the resin and purified by HPLC to obtain the product MH$^+$ 1327.

IMP 333 The peptide was made with 1 g of the same resin that was used to make IMP 332. The DTPA tetra-t-butyl ester (U.S. Publ. No. 20050002945) was added to both of the amines of the Dpr group. The Aloc groups were then removed and the Trt-HSG-OH was added. The peptide was then cleaved and purified by HPLC to obtain the desired product MH$^+$ 1845.

IMP 334 The peptide was made on 1 g Rink amide resin (0.7 mmol/g) with the following amino acids added in the order shown: Fmoc-D-Lys(Aloc)-OH, Fmoc-D-Glu(But)-OH, Fmoc-D-Lys(Aloc)-OH, Boc-Ser(But)-OH, The Aloc groups were removed and the Trityl-HSG-OH was added. The peptide was cleaved from the resin with TFA. The crude peptide was collected by precipitation from ether and dried. Sodium periodate, 0.33 g, was dissolved in 15 mL water. The crude peptide was dissolved in 1 ml, 0.5 M sodium phosphate pH 7.6, 3 mL water and 1 mL of the periodate solution. 3 mL more periodate in one milliliter increments was added over 2 hr. The mixture was then purified by reverse phase HPLC and lyophilized to obtain the aldehyde IMP 289 HCO—CO-D-Lys(HSG)-D-Glu-D-Lys(HSG)-NH$_2$ MH$^+$ 959. Alendronate (0.0295 g, CALBIOCHEM®) was dissolved in 150 μL 0.1 M NaOAc pH 4. The peptide, IMP 289, (0.0500 g) was dissolved in 100 μL of 13% isopropanol in water. Sodium cyanoborohydride was added and the mixture was purified by HPLC to afford the desired product MH$^+$ 1192.

IMP 337 & IMP 338 The peptide was made on Sieber amide resin using the following amino acids added in the order shown: Fmoc-D-Lys(Aloc)-OH, Fmoc-D-Ala-OH, Fmoc-D-Lys(Aloc)-OH, Fmoc-D-Ala-OH, Fmoc-D-Ser(PO(OBzl)OH)—OH, Fmoc-D-Ser(PO(OBzl)OH)—OH, and Ac$_2$O. The Aloc groups were removed and the Trt-HSG-OH groups were added to the side chains of the lysines. The peptide was cleaved from the resin and purified by HPLC to afford the desired products: IMP 337 MH⁺ 1291 and IMP 338 MH⁺ 1126.

IMP 345 The peptide was made on Sieber amide Resin using the following amino acids added in the order shown: Fmoc-D-Lys(Aloc)-OH, Fmoc-D-Ala-OH, Fmoc-D-Lys (Aloc)-OH, Fmoc-D-Ala-OH, Fmoc-D-Ser(PO(OBzl)OH)—OH, and tetra-t-butyl DTPA. The Aloc groups were removed and the Trt-HSG-OH groups were added to the side chains of the lysines. The peptide was cleaved from the resin and purified by HPLC to afford the desired product: IMP 345 MH⁺ 1459.

IMP 349 The peptide IMP 347 DTPA-D-Cys-D-Ala-D-Lys(HSG)-D-Tyr-D-Lys(HSG)-NH₂ was made on Sieber amide Resin using the following amino acids added in the order shown: Aloc-D-Lys(Fmoc)-OH, Trt-HSG-OH, the aloc was cleaved, Fmoc-D-Ala-OH, Aloc-D-Lys(Fmoc)-OH, Trt-HSG-OH were added, the aloc was cleaved Fmoc-D-Ala-OH, Fmoc-D-Cys(Trt)-OH and tetra-t-butyl DTPA were added. The peptide was cleaved from the resin and purified by HPLC to afford the desired product: IMP 347 MH⁺ 1395. The peptide, IMP 347, 0.0446 g ($3.2 \times 10^{-5}$ mol) was mixed with 0.4605 g ($2.4 \times 10^{-3}$ mol) of ethenylidenebis(phosphonic acid) (Degenhardt et al., *J. Org. Chem.* 1986, 51:3488-3490) in 3 mL of water and the solution was adjusted to pH 6.5 with 1 M NaOH added dropwise. The reaction was stirred overnight and the reaction solution was adjusted to pH 1.49 by the addition of excess ethenylidenebis(phosphonic acid). The mixture was stirred overnight at room temperature and then purified by HPLC to obtain the desired peptide IMP 349 MH⁺ 1583.

IMP 361 The peptide was made on Sieber amide resin using the following amino acids added in the order shown: Aloc-D-Lys(Fmoc)-OH, Trt-HSG-OH, the aloc was cleaved, Fmoc-D-Ala-OH, Aloc-D-Lys(Fmoc)-OH, Trt-HSG-OH were added, the aloc was cleaved, Fmoc-D-Ala-OH, Fmoc-Dap(Aloc)-OH and tetra-t-butyl DTPA were added. The Aloc on the side chain of the Dap was removed and bromo acetyl was added with bromo acetic anhydride. The crude product was purified by HPLC to obtain the desired peptide IMP 361 (MH⁺ 1498).

IMP 366 The peptide was made by the same method as IMP 361 with phenylthioacetic acid added last. The crude product was purified by HPLC to afford the product IMP 366 MH⁺ 1528.

IMP 368 The peptide was as described for IMP 349 except the cysteine residue was not added and symmetrical tetra-t-butylDTPA (MACROCYCLICS®) was used in place of the unsymmetrical DTPA to obtain the desired product after purification, IMP 368 MH⁺ 1292.

IMP 369 The peptide was made as described for IMP 349 with Fmoc-R-3-amino-3-(2-bromophenyl)propionic acid added in place of the D-Cys and symmetrical tetra-t-butylDTPA added in place of the unsymmetrical version to the DTPA tetra-t-butyl ester. The crude peptide was purified to obtain the desired product, MH⁺ 1517.

IMP 370 The peptide was made as described for IMP 369 except Fmoc-R-3-amino-3-(2-nitrophenyl) propionic acid was used instead of the bromo. The desired product was obtained after purification by HPLC MH⁺ 1484.

IMP 371 The peptide was made as described for IMP 370 except the unsymmetrical tetra-t-butyl DTPA was used in place of the of the symmetrical version. The desired product was obtained after purification by HPLC MH⁺ 1484.

IMP 372 The peptide was made as described for IMP 361 with Fmoc-Ser(But)-OH used to attach the Ser to the Dap side chain. The Fmoc was removed and the peptide was cleaved from the resin and purified to obtain the desired product MH⁺ 1465.

IMP 373 The peptide was made as described for IMP 361 with symmetrical-tetra-t-butylester DTPA used to attach the Sym-DTPA to the Dap side chain. The peptide was cleaved from the resin and purified to obtain the desired product MH⁺ 1753.

IMP 374 The peptide was made as described for IMP 361 with Fmoc-S-ethyl cysteine added to the Dap side chain followed by chloro acetyl (on the cysteine nitrogen) added via chloroacetic anhydride. The peptide was cleaved from the resin and purified to obtain the desired product MH⁺ 1585.

IMP 375 The peptide was made as described for IMP 361 with Fmoc-R-3-amino-3-(2-bromophenyl)propionic acid added to the Dap side chain followed by cleavage of the Fmoc group. The peptide was cleaved from the resin and purified to obtain the desired product MH⁺ 1603.

IMP 376 The peptide was made as described for IMP 361 with Fmoc-D-Tyr(But)-OH added after the second alanine followed by Fmoc-Cys(SO₃H) and tetra-t-butylDTPA. The peptide was cleaved from the resin and purified to obtain the desired product MH⁺ 1558.

IMP 379 The peptide was made as described for IMP 361 with Boc-2-Abz-OH added to the side chain of the Dap. The peptide was cleaved from the resin and purified to obtain the desired product MH⁺ 1497.

IMP 382 The peptide was made as described for IMP 361 with the Aloc removed from the side chain of the Dap. The peptide was cleaved from the resin and purified to obtain the desired product MH⁺ 1378.

IMP 383 The peptide was made as described for IMP 361 with Fmoc-Gla(OBut)₂-OH added to the side chain of the Dap. The peptide was cleaved from the resin and purified to obtain the desired product MH⁺—CO₂ 1507.

IMP 384 The peptide was made as described for IMP 361 with Fmoc-Boc-S-3-amino-3-(2-hydroxyphenyl)propionic acid added to the side chain of the Dap. The peptide was cleaved from the resin and purified to obtain the desired product MH⁺ 1541.

IMP 385 The peptide was made as described for IMP 361 with Fmoc-Dpr(Fmoc)-OH added to the side chain of the Dap. The peptide was cleaved from the resin and purified to obtain the desired product MH⁺ 1464.

IMP 386 The peptide was made as described for IMP 361 with Boc-D-2-pyridylalanine-OH added to the side chain of the Dap. The peptide was cleaved from the resin and purified to obtain the desired product MH⁺ 1526.

IMP 387 The peptide was made as described for IMP 361 with Fmoc-D-9-anthrylalanine-OH added to the side chain of the Dap. The peptide was cleaved from the resin and purified to obtain the desired product MH⁺ 1625.

IMP 389 The peptide was made as described for IMP 361 with bis-Boc-piperazine-2-carboxylate added to the side chain of the Dap. The peptide was cleaved from the resin and purified to obtain the desired product MH+ 1664.

Example 5

In-Vivo Studies

Nude mice bearing GW-39 human colonic xenograft tumors (100-500 mg) are injected with the bispecific antibody hMN-14×m679 ($1.5\times10^{-10}$ mol). The antibody is allowed to clear for 24 hr before the F-18 labeled peptide (8.8 µCi, $1.5\times10^{-11}$ mol) is injected. The animals are imaged at 3, 24 and 48 hr post injection. The xenograft tumors are clearly imaged by PET scanning detection of the F-18 labeled peptide bound to the bispecific hMN-14×m679 that is localized to the tumors by binding of hMN-14 to tumor antigen.

Example 6

Production and Use of a Serum-Stable F-18 Labeled Peptide

IMP 449 NOTA-ITC benzyl-D-Ala-D-Lys(HSG)-D-Tyr-D-Lys(HSG)-NH$_2$ MH+ 1459

The peptide, IMP 448 D-Ala-D-Lys(HSG)-D-Tyr-D-Lys(HSG)-NH$_2$ MH+ 1009 was made on Sieber Amide resin by adding the following amino acids to the resin in the order shown: Aloc-D-Lys(Fmoc)-OH, Trt-HSG-OH, the Aloc was cleaved Fmoc-D-Tyr(But)-OH, Aloc-D-Lys(Fmoc)-OH, Trt-HSG-OH, the Aloc was cleaved, Fmoc-D-Ala-OH with final Fmoc cleavage to make the desired peptide. The peptide was then cleaved from the resin and purified by HPLC to produce IMP 448, which was then coupled to ITC-benzyl NOTA. The peptide, IMP 448, 0.0757 g ($7.5\times10^{-5}$ mol) was mixed with 0.0509 g ($9.09\times10^{-5}$ mol) ITC benzyl NOTA and dissolved in 1 mL water. Potassium carbonate anhydrous, 0.2171 g was then slowly added to the stirred peptide/NOTA solution. The reaction solution was pH 10.6 after the addition of all the carbonate. The reaction was allowed to stir at room temperature overnight. The reaction was carefully quenched with 1 M HCl after 14 hr and purified by HPLC to obtain 48 mg of IMP 449 the desired product.

35% (RT ~10 min) of the activity was attached to the peptide and 65% of the activity was eluted at the void volume of the column (3.1 min) indicating that the activity was not associated with the peptide. The crude labeled mixture (5 µL) was mixed with pooled human serum and incubated at 37° C. An aliquot was removed after 15 min and analyzed by HPLC. The HPLC showed 9.8% of the activity was still attached to the peptide (down from 35%). Another aliquot was removed after 1 hr and analyzed by HPLC. The HPLC showed 7.6% of the activity was still attached to the peptide (down from 35%), which was essentially the same as the 15 min trace.

High Dose F-18 Labeling

Figure 19A:
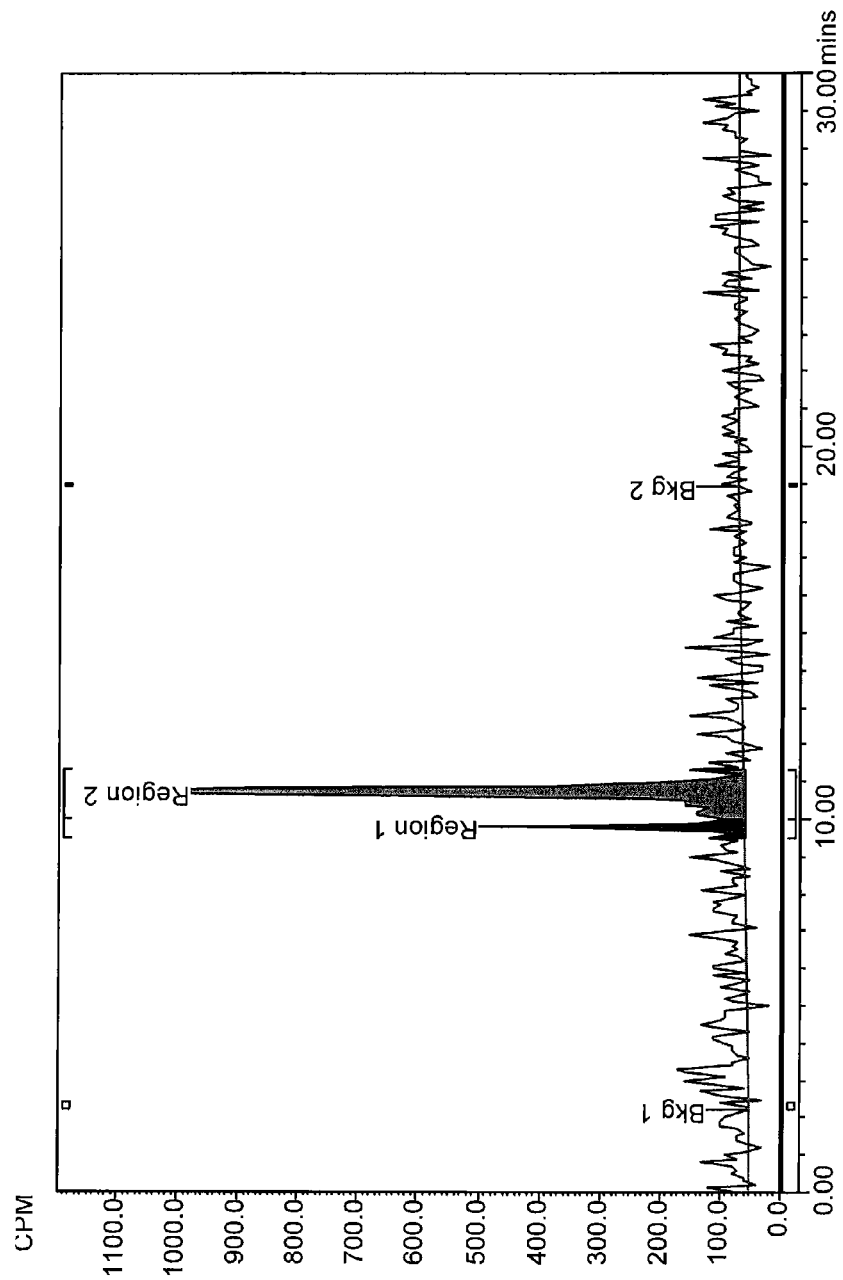
Figure 19B:
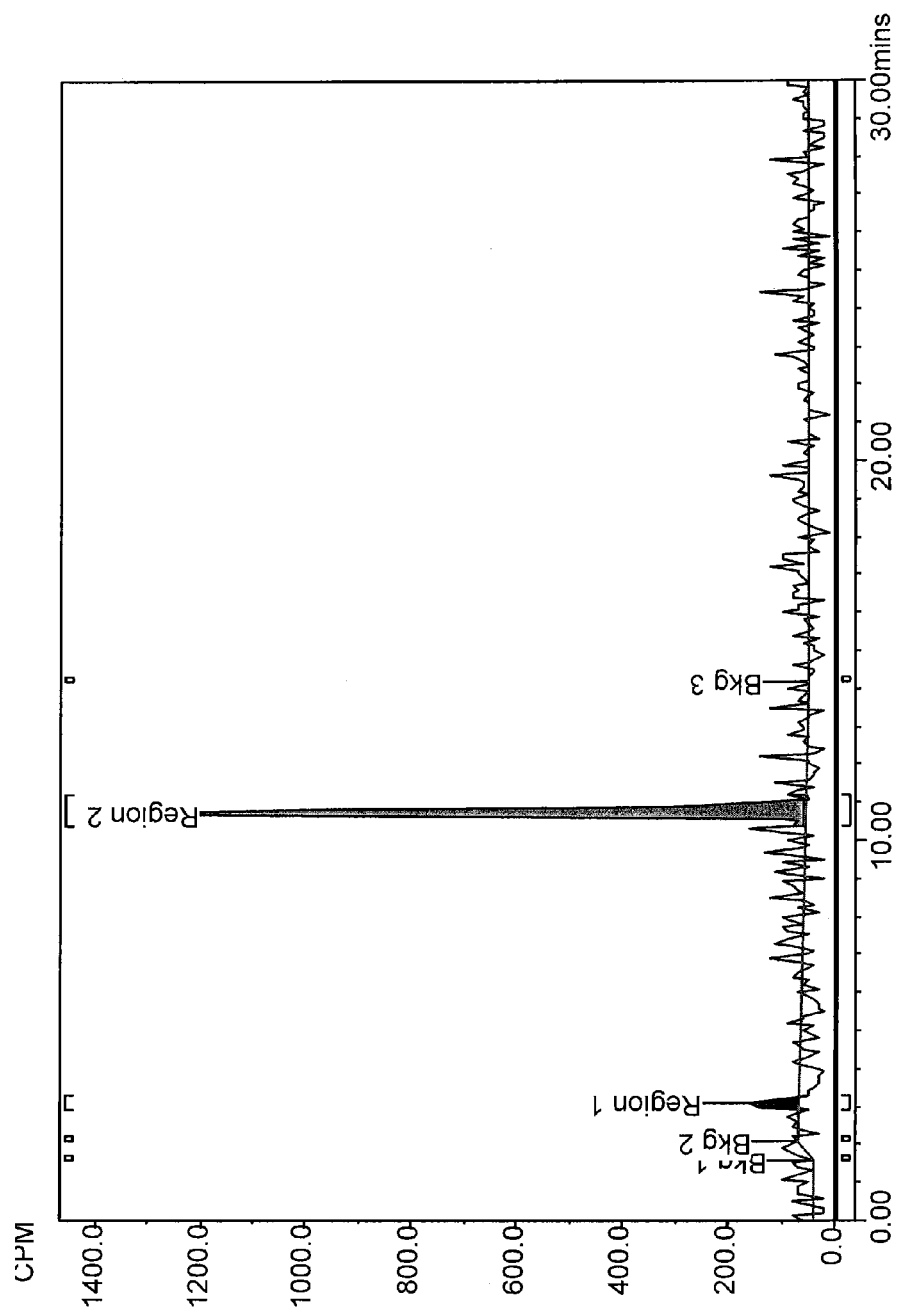
Figure 19C:
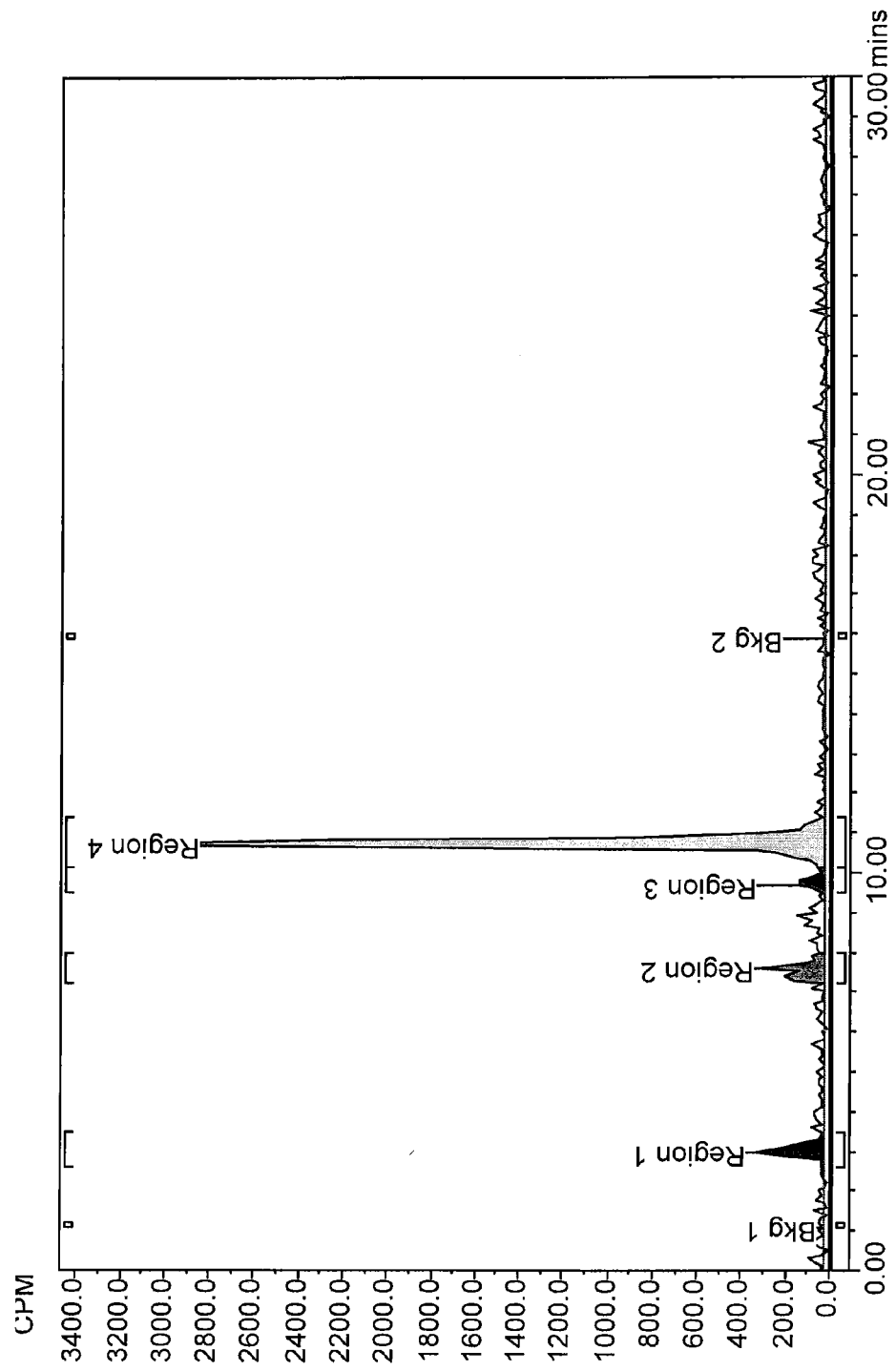
Figure 19D:
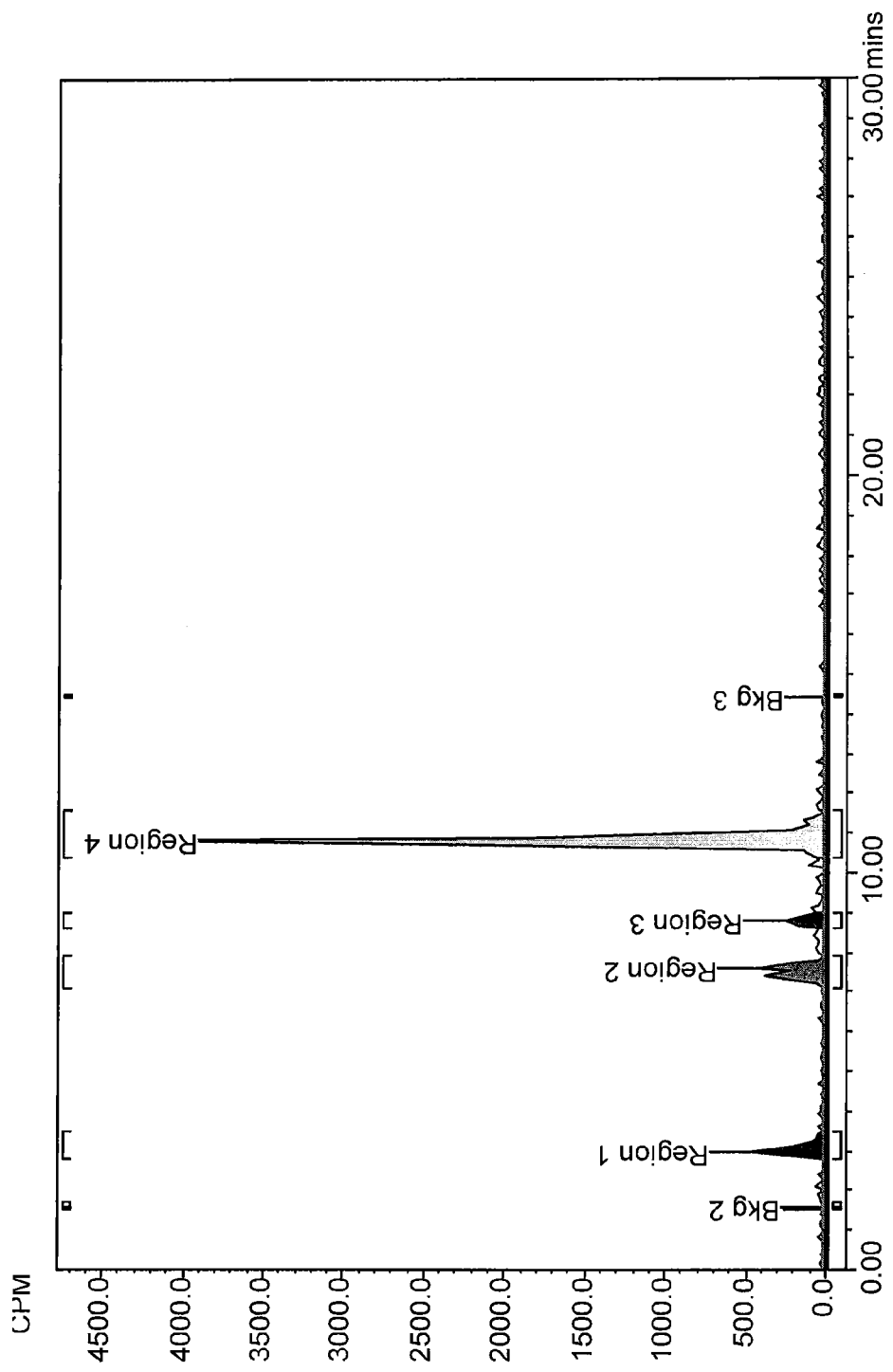

Further studies with purified IMP 449 demonstrated that the F-18 labeled peptide was highly stable (91%, FIG. 19B) in human serum at 37° C. for at least one hour and was partially stable (76%, FIG. 19D) in human serum at 37° C. for at least four hours. These results demonstrate that the F-18 labeled peptides disclosed herein exhibit sufficient stability under approximated in vivo conditions to be used for F-18 imaging studies.

F-18~21 mCi in ~400 µL of water was mixed with 9 µL of 2 mM AlCl$_3$ in 0.1 M pH 4 NaOAc. The peptide, IMP 449, 60 µL (0.01 M, $6\times10^{-7}$ mol in 0.5 NaOH pH 4.13) was added and the solution was heated to 110° C. for 15 min. The crude labeled peptide was then purified by placing the reaction solution in the barrel of a 1 cc Waters HLB column and eluting with water to remove unbound F-18 followed by 1:1 EtOH/H$_2$O to elute the F-18 labeled peptide. The crude reaction solution was pulled through the column into a waste vial and the column was washed with three one milliliter fractions of water (18.97 mCi). The HLB column was then placed on a new vial and eluted with two×200 µL 1:1 EtOH/H$_2$O to collect the labeled peptide (1.83 mCi). The column retained 0.1 mCi of activity after all of the elutions were complete. An aliquot of the purified F-18 labeled peptide (20 µL) was mixed with 200 µL of pooled human serum and heated at 37° C. Aliquots were analyzed by reverse phase HPLC (as described above). The results show the relative stability of F-18 labeled purified IMP 449 at 37° C. at time zero (FIG. 19A), one hour (FIG. 19B, 91% labeled peptide), two hours (FIG. 19C, 77%

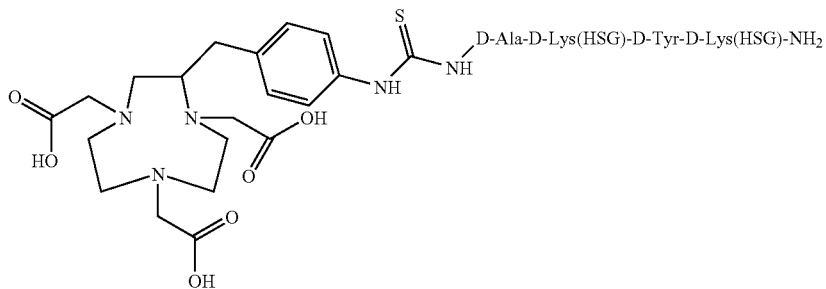

F-18 Labeling of IMP 449

The peptide, 0.002 g ($1.37\times10^{-6}$ mol) was dissolved in 686 µL (2 mM peptide solution) 0.1 M NaOAc pH 4.02. Three microliters of a 2 mM solution of Al in a pH 4 acetate buffer was mixed with 15 µL, 1.3 mCi of F-18. The solution was then mixed with 20 µL of the 2 mM IMP 449 solution and heated at 105° C. for 15 min. Reverse Phase HPLC analysis showed labeled peptide) and four hours (FIG. 19D, 76% labeled peptide) of incubation in human serum. It was also observed that F-18 labeled IMP 449 was stable in TFA solution, which is occasionally used during reverse phase HPLC chromatography. There appears to be a general correlation between stability in TFA and stability in human serum observed for the exemplary F-18 labeled molecules described herein.

What is claimed is:

1. A method of F-18 imaging by positron emission tomography (PET) comprising:
   a) activating F-18 by addition of a group IIIA element to form an F-18 group IIIA element complex;
   b) attaching the complex to a protein or peptide to form an F-18 labeled protein or peptide, wherein the F-18 group IIIA complex attaches to a chelating moiety on the protein or peptide;
   c) administering the labeled protein or peptide to a subject; and
   d) imaging the distribution of the F-18 labeled protein or peptide by PET scanning.

2. The method of claim 1, wherein the F-18 labeled protein or peptide is administered to the subject without purifying the F-18 labeled protein or peptide from unlabeled protein or peptide.

3. The method of claim 2, wherein the complex is attached to the protein or peptide without purifying F-18 containing complex from uncomplexed F-18.

4. The method of claim 1 wherein the F-18 labeled protein or peptide is used to image receptors.

5. The method of claim 1 wherein the F-18 labeled protein or peptide is used to image tumors.

6. The method of claim 1 wherein the F-18 labeled protein or peptide is targeted using antibodies, antibody fragments, or antibody constructs.

7. The method of claim 1 where the F-18 labeled protein or peptide is targeted using bispecific antibodies.

8. The method of claim 7, further comprising:
   i) administering a bispecific antibody to a subject, said bispecific antibody having at least one binding site for a targetable construct and at least one binding site for a targeted antigen, wherein the presence of the targeted antigen is indicative of a disease or condition;
   ii) allowing a sufficient amount of time for bispecific antibody that is not bound to the targeted antigen to clear from circulation; and
   iii) administering an F-18 labeled targetable construct to the subject.

9. The method of claim 8, wherein the targeted antigen is a tumor-associated antigen.

10. The method of claim 8, wherein the targeted antigen is present on a pathogenic organism.

11. The method of claim 10, wherein the pathogen is a virus, bacterium, fungus, yeast or microorganism.

12. The method of claim 8, wherein the targeted antigen is selected from the group consisting of colon-specific antigen-p (CSAp), carcinoembryonic antigen (CEA), CD4, CD5, CD8, CD14, CD15, CD19, CD20, CD21, CD22, CD23, CD25, CD30, CD45, CD74, CD80, HLA-DR, Ia, Ii, MUC 1, MUC 2, MUC 3, MUC 4, NCA, EGFR, HER 2/neu receptor, TAG-72, EGP-1, EGP-2, A3, KS-1, Le(y), S100, PSMA, PSA, tenascin, folate receptor, VEGFR, EGFR, PDGFR, FGFR, P1GF, ILGF-1, necrosis antigens, IL-2, IL-6, T100, MAGE, or a combination of these antigens.

13. The method of claim 1, wherein the F-18 labeled molecule is a peptide.

14. The method of claim 13, wherein the peptide is selected from the group consisting of IMP 272, IMP 332, IMP 333, IMP 361, IMP 366, IMP 371, IMP 372, IMP 373, IMP 374, IMP 375, IMP 376, IMP 379, IMP 382, IMP 383, IMP 384, IMP 385, IMP 386, IMP 387, IMP 389 and IMP 449.

15. The method of claim 13, wherein the peptide is IMP 449.

16. The method of claim 1, wherein the chelating moiety is selected from the group consisting of NOTA, DTPA, 2-benzyl-DTPA, TETA, NETA, a macrocyclic polyether, a porphyrin, Tscg-Cys and Tsca-Cys.

17. The method of claim 16, wherein the chelating group is NOTA.

18. The method of claim 1, wherein the group IIIA element is selected from the group consisting of aluminum, gallium, indium and thallium.

19. The method of claim 18, wherein the group IIIA element is aluminum.

20. The method of claim 13, wherein the F-18 labeled molecule is stable in human serum at 37° C. for at least 1 hour.

21. The method of claim 20, wherein the F-18 labeled molecule is stable in human serum at 37° C. for at least 4 hours.

* * * * *